(12) United States Patent
Inoue

(10) Patent No.: US 9,133,098 B2
(45) Date of Patent: Sep. 15, 2015

(54) PROCESS FOR PRODUCING ORGANOLITHIUM COMPOUND AND PROCESS FOR PRODUCING SUBSTITUTED AROMATIC COMPOUND

(71) Applicant: Nippon Soda Co., Ltd., Chiyoda-ku, Tokyo (JP)

(72) Inventor: Hiroki Inoue, Takaoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 14/506,076

(22) Filed: Oct. 3, 2014

(65) Prior Publication Data

US 2015/0025276 A1 Jan. 22, 2015

Related U.S. Application Data

(62) Division of application No. 12/998,715, filed as application No. PCT/JP2009/007286 on Dec. 25, 2009, now Pat. No. 8,871,970.

(30) Foreign Application Priority Data

Dec. 25, 2008 (JP) ................. 2008-329632

(51) Int. Cl.
*C07C 215/00* (2006.01)
*C07C 211/00* (2006.01)
*C07C 217/08* (2006.01)
*C07F 1/02* (2006.01)
*C07F 5/02* (2006.01)
*C07C 211/14* (2006.01)

(52) U.S. Cl.
CPC ............ *C07C 217/08* (2013.01); *C07C 211/14* (2013.01); *C07F 1/02* (2013.01); *C07F 5/025* (2013.01)

(58) Field of Classification Search
CPC .......................... C07C 217/08; C07C 211/512
USPC .................................................. 564/508, 512
See application file for complete search history.

(56) References Cited

U.S. PATENT DOCUMENTS

| | | | |
|---|---|---|---|
| 3,663,585 A | 5/1972 | Langer, Jr. | |
| 3,737,458 A * | 6/1973 | Langer ..................... | 564/374 |
| 4,078,019 A | 3/1978 | Langer, Jr. | |
| 4,970,342 A | 11/1990 | Fauss et al. | |
| 6,207,835 B1 | 3/2001 | Reiffenrath et al. | |
| 7,572,927 B2 | 8/2009 | Yoshida et al. | |

FOREIGN PATENT DOCUMENTS

| | | | |
|---|---|---|---|
| DE | 102 43 618 A1 | | 6/2003 |
| DE | 10243618 A1 * | | 6/2003 |
| JP | 06-256257 A | | 9/1994 |
| JP | 10-059980 A | | 3/1998 |
| JP | 2000-229981 A | | 8/2000 |
| JP | 2003-286279 A | | 10/2003 |
| JP | 2006-241065 A | | 9/2006 |
| JP | 2007-262151 A | | 10/2007 |
| JP | 2008-195639 A | | 8/2008 |

OTHER PUBLICATIONS

Andrews et al., "Solid-State Structures and Racemization of Lithiated Schöllkopf's Bis[Lactim Ehter]," Helvetica Chimica Acta, 2002, 85(10):3516-3524.
Andrianarison et al. "Lithiiertes Di-t-butylfluorsilylmesitylphosphan—vom Phosphan zum Phosphid," Journal of Organometallic Chemistry, 1990, 381(2):C38-C42.
Cotter et al., "Development and Application of a Direct Vinyl Lithiation of cis-Stilbene and a Directed Vinyl Lithiation of an Unsymmetrical cis-Stilbene," Organic Letters, 2007, 9(8):1493-1496.
Decision of Rejection dated Aug. 13, 2013 in JP 2010-543919, with English translation.
Hickey et al., "Process Development and Pilot Plant Synthesis of Methyl 2-Bromo-6-chlorobenzoate," Organic Process Research & Development, 2005, 9:764-767.
Inoue et al., "Asymmetric 1,2-Addition of Organolithiums to Aldimines Catalyzed by Chiral Ligand," Tetrahedron, 1994, 50(15):4429-4438.
International Search Report mailed Feb. 9, 2010, in PCT/JP2009/007286, 2 pages.
Jones et al., "Asymmetric Addition of Organolithium Reagents to Imines Favouring (S)-Amines," Tetrahedron Letters, 1995, 36(43):7885-7888.
Leroux et al., "N-(4-Biphenylmethyl)imidazoles as Potential Therapeutics for the Treatment of Prostate Cancer: Metabolic Robustness Due to Fluorine Substition?" Helvetica Chimica Acta, 2003, 86:2671-2686.
Noyori, Ryoji, Eds., et al., "Lecture of Graduated School: Organic Chemistry I, Molecular Structure and Reaction/Organometallic Chemistry," Jun. 25, 1999, 320-321, with English translation, one page.
Office Action dated Dec. 11, 2012, in KR 10-2011-7012688, with English translation.
Office Action dated Jun. 26, 2014, in CN 200980150184.7, with English translation.
Office Action dated May 14, 2013, in JP 2010-543919, with English translation.
Office Action dated Oct. 7, 2013, in EP 09834520.0.
Scott et al., "Preparation, Thermal Stability and Carbonyl Addition Reactions of 2,5-Difluorophenyl Lithium and 2,5-Difluorophenyl Grignard," Synlett, 2004, 9:1646-1648.

(Continued)

*Primary Examiner* — Porfirio Nazario Gonzalez
*Assistant Examiner* — Kofi Adzamli
(74) *Attorney, Agent, or Firm* — Foley & Lardner LLP

(57) ABSTRACT

A method for producing an organolithium compound includes the step of reacting an aromatic compound or a halogenated unsaturated aliphatic compound and a lithiating agent in the presence of a coordinating compound containing three or more elements having a coordinating ability in a molecule, at least one thereof being a nitrogen element, or a coordinating compound containing three or more oxygen elements having a coordinating ability in a molecule, at least one of the groups containing the oxygen elements having a coordinating ability being a tertiary alkoxy group, at a temperature of −40° C. to 40° C.

1 Claim, No Drawings

(56) References Cited

OTHER PUBLICATIONS

Sommer et al., "Synthesis of Aryllithium Compounds in a CYTOS® Lab System," Chemfiles, 2005, 5(7):12-13.

Thurner et al., "N,N,N',N',N"—Pentamethyldipropylenetriamine (PMDPTA): A Versatile Auxiliary for Site Selected Lithiation Reactions," Synthetic Communications, 1998, 28(3):443-449.

Wang et al., "Noncryogenic I/Br-Mg Exchange of Aromatic Halides Bearing Sensitive Functional Groups Using i-PrMgCl-Bis[2-(N,N-dimethylamino)ethyl] Ether Complexes," Organic Letters, 2006, 8(2):305-307.

Wu et al., "Stabilizing N-tosyl-2-lithioindiles with bis(N,N'-dimethylaminoethyl)ether-a non-cryogenic procedure for lithiation of N-tosylindoles and subsequent addition to ketones," Organic Letters, 2006, 8(2):305-307.

Zbinden et al., "Dose-dependent antithrombotic activity of an orally active tissue factor/factor VIIa inhibitor without concomitant enhancement of bleeding propensity," Bioorganic & Medicinal Chemistry, 2006, 14:5357-5369.

Office Action dated Nov. 25, 2014, in EP 09834520.0.

Leroux et al., "N-(4-Biphenylmethyl)imidazoles as Potential Therapeutics for the Treatment of Prostate Cancer: Metabolic Robustness Due to Fluorine Substitution?" Helvetica Chimica Acta, 2003, 86:2671-2686.

Office Action dated Nov. 12, 2012, in KR 10-2011-7012688, with English translation.

Thurner et al., "N,N,N',N',N"—Pentamethyldipropylenetriamine (PMDPTA): A Versatile Auxiliary for Site Selective Lithiation Reactions," Synthetic Communications, 1998, 28(3):443-449.

Wu et al., "Stabilizing N-tosyl-2-lithioindoles with bis(N,N'-dimethylaminoethyl)ether-a non-cryogenic procedure for lithiation of N-tosylindoles and subsequent addition to ketones," Tetrahedron Letters, Oct. 7, 2009, 50(40):5667-5669.

Office Action issued Dec. 16, 2014 in CN 200980150184.7, with English translation.

Ramirez et al., "Hemilabile Ligands in Organolithium Chemistry: Substituent Effects on Lithium Ion Chelation," J. Am. Chem. Soc., 2003, 125:15376-15387.

Reich et al., "Amine- and Ether-Chelated Aryllithium Reagents—Structure and Dynamics," J. Am. Chem. Soc., 2003, 125:3509-3521.

* cited by examiner

PROCESS FOR PRODUCING ORGANOLITHIUM COMPOUND AND PROCESS FOR PRODUCING SUBSTITUTED AROMATIC COMPOUND

CROSS-REFERENCE TO RELATED APPLICATIONS

This application is a Divisional of U.S. Ser. No. 12/998,715, which is the U.S. National Stage application of PCT/JP2009/007286, filed Dec. 25, 2009, which claims priority from Japanese Patent Application No. 2008-329632, filed on Dec. 25, 2008, the entire contents of which are incorporated herein by reference.

TECHNICAL FIELD

The present invention relates to a process for producing an organolithium compound and a process for producing a substituted aromatic compound, and more particularly to a method for producing an organolithium compound which is suitable for use in a reaction with an electrophilic compound, and a method for producing a substituted aromatic compound by a reaction of an organolithium compound with an electrophilic compound.

BACKGROUND ART

Substituted aromatic compounds such as aromatic amines, aromatic ethers, aromatic aldoximes and aromatic aldehydes are useful as biologically active substances (pharmaceuticals, agricultural chemicals), functional materials (liquid crystal materials, electronic materials, optical materials, photographic additives, resins, dyes and the like) or intermediates for the synthesis thereof.

There is generally known, as a method for producing a substituted aromatic compound, a method in which an aromatic compound is metalized with lithium, sodium, magnesium or the like to obtain an arylmetal compound, and then the arylmetal compound is reacted with an electrophilic compound. Also, metalization of a halogenated unsaturated aliphatic compound is similarly known.

Among metals used for metalization of such aromatic compounds and halogenated unsaturated aliphatic compounds, lithium is applied for the synthesis of various compounds from the viewpoint of a wide range of the applicable aromatic compounds and halogenated unsaturated aliphatic compounds, high reactivity and the like.

For example, Patent Document 1 discloses a method for producing an organic charge transporting polymer, which includes the step of lithiating a dihalide of N-(substituted) phenylcarbazole with an alkyl lithium and then reacting with boron trihalide.

Patent Document 2 discloses a producing method in which 4-substituted-2,6-difluorobenzene having an acetal group is lithiated with an alkyl lithium and then reacted with carbon dioxide to obtain a benzoic acid derivative and acid amide, which are then dehydrated.

It is also known that coordinating compounds such as tetramethylethylenediamine, tetramethylpropylenediamine and pentamethyldiethylenetriamine or the like are used so as to activate an organolithium reagent and an organolithium compound. These coordinating compounds may be sometimes chelate-coordinated with an organolithium compound thereby releasing the association state, thus improving the reactivity of the organolithium compound (see, for example, Non-Patent Document 1). However, the addition of these coordinating compounds improves the reactivity of a lithiated compound to be generated, while it causes severe deterioration of the stability. For example, Non-Patent Document 2 discloses that, although a lithiated compound is generated from 1,4-difluorobenzene and n-butyl lithium, the addition of tetramethylethylenediamine causes severe deterioration of the stability of a lithiated compound when compared with the case of no addition.

In metalization by lithium and subsequent introduction of an electrophile, the reaction has been carried out under very low temperature conditions (for example, −60° C. or lower and the like) so as to suppress the reactivity of a highly active organolithium compound (see, for example, Non-Patent Document 3 and Non-Patent Document 5), because it is considered that the yield of an organolithium compound or a substituted aromatic compound is considerably decreased when metalization by lithium is carried out under mild temperature conditions (for example, −20° C. to room temperature). In fact, in metalization by lithium under mild temperature conditions in the presence of tetramethylethylenediamine, the product showed low stability and a low yield (see Comparative Example 2 shown below).

Furthermore, since a reaction of an organolithium compound with an electrophilic compound is accompanied by heat generation, there was a large problem that a special facility such as a liquid nitrogen bubbling device for cooling so as to achieve a high yield of a substituted aromatic compound is required, resulting in high production cost (see, for example, Non-Patent Document 4). Moreover, in the production at industrial scale, there exist burdens in safety measures, for example, limitation on the use amount of organolithium compound, difficulty in control of an exothermic reaction and the like (paragraphs [0011] and [0012] of Patent Document 3).

As described above, in the metalization of an organic compound by lithium and the production of a substituted aromatic compound by introduction of an electrophile into an organolithium compound, there existed the need of the execution of the reaction under very low temperature conditions, and burdens in production costs and safety measures.

Recently, intense interest has been shown towards a method in which metalization by lithium is carried out using a tubular flow type reactor such as a microreactor.

For example, Patent Document 3 describes a production method in which an arylmetal compound is produced in a continuous flow type reactor in the case of producing an arylmetal compound by deprotonation of an aromatic compound having a hydrogen atom at the ortho-position to a halogen atom or a trifluoromethoxy group, or a halogen-metal exchange of a haloaromatic compound using a metalizing reagent, and reacting an arylmetal compound with an electrophilic reagent. However, this method has such a drawback that cooling costs considerably increase since the synthesis of an arylmetal compound in a continuous flow type reactor and the reaction of an arylmetal compound with an electrophilic reagent must be carried out at very low temperature of about −70° C. to −35° C.

Patent Document 4 describes a method for producing a compound useful for drugs, agricultural chemicals, liquid crystals, electrophotographies, dyes and the like, in which a halogen compound is reacted with a lithium reagent for very short residence time to obtain an organolithium compound having an aromatic ring, and then the organolithium compound is reacted with an electrophilic compound immediately before the organolithium compound causes a side reaction such as decomposition.

Patent Document 5 describes a method for producing an o-substituted aromatic compound in which lithiation and electrophilic substitution are carried out by a microreactor. This production method discloses that a chelating agent such as tertiary amine can be added so as to activate an organolithium reagent and an organolithium compound.

These methods provide the possibility of carrying out the synthesis of an organolithium compound which becomes unstable unless the synthesis is carried out under very low temperature conditions and the reaction of the organolithium compound with an electrophile under mild temperature conditions of 0° C. or higher in some cases. However, these methods require a special mixer such as a micromixer. It is also required to precisely control the residence time in a microtube within a very short time of 0.001 to 5 seconds, and a high-performance liquid feeding device is required because of a large pressure loss of a microreactor.

Also, an enormous number of microreactors are required so as to produce a large amount of the objective product because of the very small volume per one reactor usable in the production, and thus high facility costs are required. Furthermore, countermeasures against the phenomenon such as occlusion of a tube and a reactor may become necessary.

As described above, in the continuous flow type reactor (including a microreactor), the operational burden and the burden of safety measures, such as precise control of the residence time and occlusion of the tube tend to increase, which may become large obstacles of commercialization.

[Patent Document 1]
 Japanese Unexamined Application, First Publication No. 2007-262151
[Patent Document 2]
 Japanese Unexamined Application, First Publication No. 2003-286279
[Patent Document 3]
 Japanese Unexamined Application, First Publication No. 2000-229981
[Patent Document 4]
 Japanese Unexamined Application, First Publication No. 2006-241065
[Patent Document 5]
 Japanese Unexamined Application, First Publication No. 2008-195639
[Non-Patent Document 1]
 Edited by Ryoji Noyori et al., "Lecture of Graduated School: Organic Chemistry I, Molecular Structure and Reaction/Organometallic Chemistry", page 320
[Non-Patent Document 2]
 Scott, J. P.; Berwer, S. E.; Davies, A. J.; Brands, K. M. J. "Preparation, thermal stability and carbonyl addition reactions of 2,5-difluorophenyl lithium and 2,5-difluorophenyl grignard" Synlett 2004, 1646
[Non-Patent Document 3]
 Zbinden, K. G.; Banner, D. W.; Hilpert, K.; Himber, J.; Lave, T.; Riederer, M. A.; Stahl, M.; Tschopp, T. B.; Obst-Sander, U.; Bioorganic & Medicinal Chemistry 2006, 14, 5357
[Non-Patent Document 4]
 "Process Development and Pilot Plant Synthesis of Methyl 2-Bromo-6-chlorobenzoate" Organic Process Research & Development 2005, 9, 764-767
[Non-Patent Document 5]
 LerouX, F.; Hutschenreuter, T. U.; Charriere, C.; Scopelliti, R.; Hartmann, R. W. Helvetica Chimica Acta 2003, 86, 2671.

SUMMARY OF INVENTION

Technical Problem

An object of the present invention is to provide a method capable of obtaining an organolithium compound or a substituted aromatic compound in a high yield by considerably decreasing the operational burden and the burden of safety measures under comparatively mild temperature conditions.

Solution to Problem

The present invention includes the following aspects.
(1) A method for producing an organolithium compound, which includes the step of reacting an aromatic compound or a halogenated unsaturated aliphatic compound and a lithiating agent in the presence of a coordinating compound containing three or more elements having a coordinating ability in a molecule, at least one thereof being a nitrogen element, or a coordinating compound containing three or more oxygen elements having a coordinating ability in a molecule, at least one of the groups containing the oxygen elements having a coordinating ability being a tertiary alkoxy group, at a temperature of −40° C. to 40° C.
(2) The method for producing an organolithium compound according to (1), wherein the coordinating compound is a compound represented by formula (1):

Chemical Formula 1

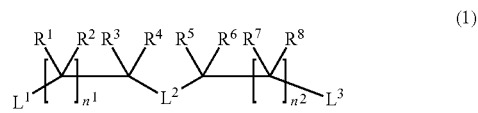

(1)

wherein, in formula (1), $L^1$, $L^2$, and $L^3$ each, independently, represents a group having an oxygen element or a group having an nitrogen element (provided that at least one of $L^1$, $L^2$, and $L^3$ is a group having an nitrogen element) or $L^1$, $L^2$, and $L^3$ each, independently, represents a group having an oxygen element (provided that at least one of $L^1$ and $L^3$ is a tertiary alkoxy group), $n^1$ and $n^2$ each, independently, represents an integer of 1 to 3, $R^1$ to $R^8$ each, independently, represents a hydrogen atom, an alkyl group, an aryl group, or a heteroaryl group, and may form a ring between ($R^1$ or $R^2$) and ($R^3$ or $R^4$), or may form a ring between ($R^5$ or $R^6$) and ($R^7$ or $R^8$), or may form a ring between ($R^3$ or $R^4$) and ($R^5$ or $R^6$), or may form a ring between ($R^1$ or $R^2$) and $L^1$, or may form a ring between ($R^7$ or $R^8$) and $L^3$.
(3) The method for producing an organolithium compound according to (1), wherein the coordinating compound is a compound represented by formula (2):

Chemical Formula 2

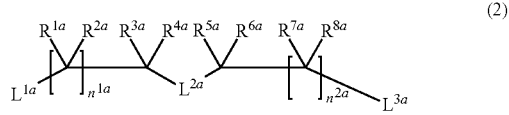

(2)

wherein, in formula (2), $L^{2a}$ represents —O— or —N(—$CH_2$—$R^{11}$)—, $R^{11}$ represents a hydrogen atom or a C1-6 alkyl group, $L^{1a}$ represents —$OR^{12}$ or —$N(R^{13})R^{14}$, $L^{3a}$ represents —$OR^{121}$ or —$N(R^{131})R^{141}$, $R^{12}$ and $R^{121}$ each, independently, represents a C1-6 alkyl group, $R^{13}$ and $R^{131}$ each, independently, represents a methyl group, an ethyl group, or an n-propyl group, $R^{14}$ and $R^{141}$ each, independently, represents a C1-6 alkyl group (provided that, when $L^{2a}$ is —O— and $L^{1a}$ is —$OR^{12}$, $L^{3a}$ is —$N(R^{121})R^{141}$ and, when $L^{2a}$ is —O— and $L^{3a}$ is —$OR^{121}$, $L^{1a}$ is —$N(R^{13})R^{14}$), $n^{1a}$ and $n^{2a}$ each, independently, represents an integer of 1 to 3, $R^{1a}$ to $R^{8a}$ each, independently, represents a hydrogen atom, a C1-6 alkyl group, or a phenyl group and may form a ring between ($R^{1a}$ or $R^{2a}$) and ($R^{3a}$ or $R^{4a}$) or may form a ring between ($R^{5a}$ or $R^{6a}$) and ($R^{7a}$ or $R^{8a}$).

(4) The method for producing an organolithium compound according to any one of (1) to (3), wherein the aromatic compound is reacted with the lithiating agent in the above step.

(5) The method for producing an organolithium compound according to (4), wherein the aromatic compound and the lithiating agent are subjected to a lithiation reaction by deprotonation in the above step.

(6) A method for producing a substituted aromatic compound, which includes the steps of reacting an aromatic compound and a lithiating agent in the presence of a coordinating compound containing three or more elements having a coordinating ability in a molecule, at least one thereof being a nitrogen element, or a coordinating compound containing three or more oxygen elements having a coordinating ability in a molecule, at least one of the groups containing the oxygen elements having a coordinating ability being a tertiary alkoxy group, at a temperature of 40° C. or lower to obtain an organolithium compound, and reacting the organolithium compound obtained in the above step with an electrophilic compound at a temperature of −40° C. to 40° C.

(7) The method for producing a substituted aromatic compound according to (6), wherein the coordinating compound is a compound represented by formula (1):

Chemical Formula 3

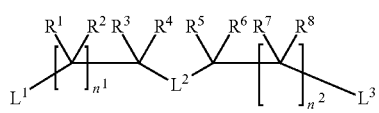

(1)

wherein, in formula (1), $L^1$, $L^2$, and $L^3$ each, independently, represents a group having an oxygen element or a group having an nitrogen element (provided that at least one of $L^1$, $L^2$, and $L^3$ is a group having an nitrogen element) or $L^1$, $L^2$, and $L^3$ each, independently, represents a group having an oxygen element (provided that at least one of $L^1$ and $L^3$ is a tertiary alkoxy group), $n^1$ and $n^2$ each, independently, represents an integer of 1 to 3, $R^1$ to $R^8$ each, independently, represents a hydrogen atom, an alkyl group, an aryl group, or a heteroaryl group, and may form a ring between ($R^1$ or $R^2$) and ($R^3$ or $R^4$), or may form a ring between ($R^5$ or $R^6$) and ($R^7$ or $R^8$), or may form a ring between ($R^3$ or $R^4$) and ($R^5$ or $R^6$), or may form a ring between ($R^1$ or $R^2$) and $L^1$, or may form a ring between ($R^7$ or $R^8$) and $L^3$.

(8) The method for producing a substituted aromatic compound according to (6), wherein the coordinating compound is a compound represented by formula (2):

Chemical Formula 4

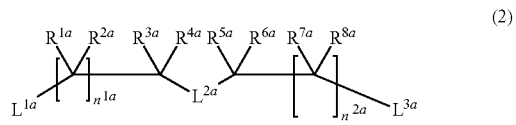

(2)

wherein, in formula (2), $L^{2a}$ represents —O— or —N(—$CH_2$—$R^{11}$)—, $R^{11}$ represents a hydrogen atom or a C1-6 alkyl group, $L^{1a}$ represents —$OR^{12}$ or —$N(R^{13})R^{14}$, $L^{1a}$ represents —$OR^{121}$ or —$N(R^{131})R^{141}$, $R^{12}$ and $R^{121}$ each, independently, represents a C1-6 alkyl group, $R^{13}$ and $R^{131}$ each, independently, represents a methyl group, an ethyl group, or an n-propyl group, $R^{14}$ and $R^{141}$ each, independently, represents a C1-6 alkyl group (provided that, when $L^{2a}$ is —O— and $L^{1a}$ is —$OR^{12}$, $L^{3a}$ is —$N(R^{131})R^{141}$ and, when $L^{2a}$ is —O— and $L^{3a}$ is —$OR^{121}$, $L^{1a}$ is —$N(R^{13})R^{14}$), $n^{1a}$ and $n^{2a}$ each, independently, represents an integer of 1 to 3, $R^{1a}$ to $R^{8a}$ each, independently, represents a hydrogen atom, a C1-6 alkyl group, or a phenyl group and may form a ring between ($R^{1a}$ or $R^{2a}$) and ($R^{3a}$ or $R^{4a}$), or may form a ring between ($R^{5a}$ or $R^{6a}$) and ($R^{7a}$ or $R^{8a}$).

(9) The method for producing a substituted aromatic compound according to any one of (6) to (8), which includes maintaining a state where the electrophilic compound is more excessive than the organolithium compound in the step of reacting the organolithium compound with the electrophilic compound.

(10) The method for producing a substituted aromatic compound according to anyone of (6) to (9), wherein the aromatic compound is reacted with the lithiating agent in the step of obtaining the organolithium compound.

(11) The method for producing a substituted aromatic compound according to (10), wherein the aromatic compound and the lithiating agent are subjected to a lithiation reaction by deprotonation in the step of obtaining the organolithium compound.

(12) Use of a coordinating compound containing three or more elements having a coordinating ability in a molecule, at least one thereof being a nitrogen element, or a coordinating compound containing three or more oxygen elements having a coordinating ability in a molecule, at least one of the groups containing the oxygen elements having a coordinating ability being a tertiary alkoxy group, in a continuous flow type reactor, as an occlusion-preventing agent or a residence time extending agent in the production of an organolithium compound, or the production of a substituted aromatic compound by a reaction of an organolithium compound with an electrophilic compound.

(13) Use of a coordinating compound containing three or more elements having a coordinating ability in a molecule, at least one thereof being a nitrogen element, or a coordinating compound containing three or more oxygen elements having a coordinating ability in a molecule, at least one of the groups containing the oxygen elements having a coordinating ability being a tertiary alkoxy group, as a reaction runaway inhibitor or a scaling inhibitor in the production of an organolithium compound, or the production of a substituted aromatic compound by a reaction of an organolithium compound with an electrophilic compound.

(14) A ligand represented by formula (3):

Chemical Formula 5

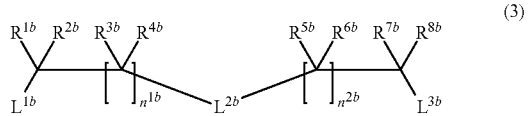

(3)

wherein, in formula (3), $L^{2b}$ represents —O— or —N(—CH$_2$—R$^{21}$)—, R$^{21}$ represents a hydrogen atom or a C1-6 alkyl group, $L^{1b}$ represents —OR$^{22}$ or —N(R$^{23}$)R$^{24}$, $L^{3b}$ represents —OR$^{221}$ or —N(R$^{231}$) R$^{241}$, R$^{22}$ and R$^{221}$ each, independently, represents a C1-6 alkyl group, R$^{23}$ and R$^{231}$ each, independently, represents a methyl group, an ethyl group, or an n-propyl group, R$^{24}$ and R$^{241}$ each, independently, represents a C1-6 alkyl group (provided that when $L^{2b}$ is —O— and $L^{1b}$ is —OR$^{22}$, $L^{3b}$ is —N(R$^{231}$)R$^{241}$ and, when $L^{2b}$ is —O— and $L^{3b}$ is —OR$^{221}$, $L^{1b}$ is —N(R$^{23}$)R$^{24}$), n$^{1b}$ and n$^{2b}$ each, independently, represents an integer of 1 to 3, R$^{1b}$ and R$^{2b}$ represent a C1-6 alkyl group, R$^{3b}$ to R$^{8b}$ each, independently, represents a hydrogen atom or a C1-6 alkyl group (provided that when $L^{2b}$ is —N—CH$_3$, $L^{1b}$ and $L^{3b}$ is —N(CH$_3$)CH$_3$ and n$^{1b}$ and n$^{2b}$ are 1, R$^{1b}$ to R$^{8b}$ are not simultaneously methyl groups) and may form a ring between (R$^{1b}$ or R$^{2b}$) and (R$^{3b}$ or R$^{4b}$) or may form a ring between (R$^{5b}$ or R$^{6b}$) and (R$^{7b}$ or R$^{8b}$).

Advantageous Effects of Invention

According to the method for producing an organolithium compound of the present invention, it is possible to considerably improve the stability of an organolithium compound produced through metalization by lithium. This method enables the production of an organolithium compound in a high yield under comparatively mild conditions by considerably decreasing the operational burden and the burden of safety measures. Also, according to the method for producing a substituted aromatic compound of the present invention, it is possible to obtain a substituted aromatic compound in a high yield under comparatively mild conditions by considerably decreasing the operational burden and the burden of safety measures. That is, in a tubular flow type reactor such as a microreactor and a cascade method, defects such as occlusion of transfer tubes among a tube, a reactor and a batch are less likely to arise in the continuous reaction under comparatively mild conditions. In the case of a batch type reaction, the generation of scaling of the reactor can be prevented and thus the reaction can be easily controlled. In case very large stabilization effect of an organolithium compound is exerted, continuation per se can be avoided. Furthermore, according to the production method of the present invention, since a special facility is not required for cooling and the like, production costs can be considerably suppressed. In a tubular flow type reactor, since the diameter of the tube can be increased, production costs can be considerably suppressed.

DESCRIPTION OF EMBODIMENTS

The present inventors have intensively studied so as to achieve the above object and found coordinating compounds such as pentamethyldiethylenetriamine, as a substance which has an ability capable of considerably suppressing decomposition, dimerization, oligomerization, polymerization and the like involved in an organolithium compound under comparatively mild temperature conditions, and also can achieve stabilization of an organolithium compound.

They have also found that the stabilization of the organolithium compound is not recognized in a bidentate compound such as tetramethylethylenediamine, and the stabilization is specifically carried out by a coordinating compound containing three or more elements having a coordinating ability in a molecule, at least one thereof being a nitrogen element, or a coordinating compound containing three or more oxygen elements having a coordinating ability in a molecule, at least one of the groups containing the oxygen elements having a coordinating ability being a tertiary alkoxy group.

They have further studied based on this finding and found that an organolithium compound can be produced in a high yield through a considerable decrease in the operational burden and the burden of safety measures, by reacting an aromatic compound or a halogenated unsaturated aliphatic compound with a lithiating agent under comparatively mild conditions in the presence of a coordinating compound containing three or more elements having a coordinating ability in a molecule, at least one thereof being a nitrogen element, or a coordinating compound containing three or more oxygen elements having a coordinating ability in a molecule, at least one of the groups containing the oxygen elements having a coordinating ability being a tertiary alkoxy group, and that substituted aromatic compound can be obtained in a high yield through a considerable decrease in the operational burden and the burden of safety measures, by reacting the organolithium compound obtained by this production method with an electrophilic compound under comparatively mild conditions.

Furthermore, they have found that defects such as occlusion of a tube, a reactor do not arise by reacting in the presence of a coordinating compound containing three or more elements having a coordinating ability in a molecule, at least one thereof being a nitrogen element, or a coordinating compound containing three or more oxygen elements having a coordinating ability in a molecule, at least one of the groups containing the oxygen elements having a coordinating ability being a tertiary alkoxy group, using a tubular flow type reactor such as a flow reactor, under comparatively mild conditions.

The present invention has been completed based on these findings.

Next, a method for producing an organolithium compound according to the first aspect of the present invention will be described.

The method for producing an organolithium compound includes the step of reacting an aromatic compound or a halogenated unsaturated aliphatic compound and a lithiating agent in the presence of a coordinating compound containing three or more elements having a coordinating ability in a molecule, at least one thereof being a nitrogen element, or a coordinating compound containing three or more oxygen elements having a coordinating ability in a molecule, at least one of the groups containing the oxygen elements having a coordinating ability being a tertiary alkoxy group, at a temperature of −40° C. to 40° C.

The coordinating compound used in the present aspect is a compound containing three of more elements having a coordinating ability in a molecule, which is coordinatable with a lithium element. Examples of elements having a coordinating ability include a nitrogen element, an oxygen element, a phosphorus element, a sulfur element and the like, and at least one of elements having a coordinating ability is a nitrogen element in the coordinating compound used in the present aspect.

Another coordinating compound used in the present aspect is a compound containing three of more oxygen elements having a coordinating ability in a molecule, which is coordinatable with a lithium element. At least one of the groups containing oxygen elements having a coordinating ability is a tertiary alkoxy group.

The coordinating compound suitable for the present aspect is preferably a compound containing a group having a coordinating ability in the tridentate, i.e. a tridentate compound. Examples of the tridentate compound include a tripodal compound (three groups having a coordinating ability are radially connected from one element) and a tandem compound (three groups having a coordinating ability are tandemly connected). In the present aspect, a tandem tridentate compound is preferable. The tandem tridentate compound is more preferably a compound represented by formula (1) or (2):

Chemical Formula 6

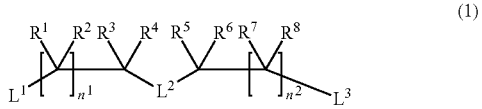

(1)

wherein, in formula (1),
$L^1$, $L^2$, and $L^3$ each, independently, represents a group having an oxygen element or a group having an nitrogen element (provided that at least one of $L^1$, $L^2$, and $L^3$ is a group having an nitrogen element) or $L^1$, $L^2$, and $L^3$ each, independently, represents group having an oxygen element (provided that at least one of $L^1$ and $L^3$ is a tertiary alkoxy group),
$n^1$ and $n^2$ each, independently, represents an integer of 1 to 3,
$R^1$ to $R^8$ each, independently, represents a hydrogen atom, an alkyl group, an aryl group, or a heteroaryl group and may form a ring between ($R^1$ or $R^2$) and ($R^3$ or $R^4$), or may form a ring between ($R^5$ or $R^6$) and ($R^7$ or $R^8$), or may form a ring between ($R^3$ or $R^4$) and ($R^5$ or $R^6$), or may form a ring between ($R^1$ or $R^2$) and $L^1$, or may form a ring between ($R^7$ or $R^8$) and $L^3$.

The alkyl group is preferably a linear, branched or cyclic alkyl group of 1 to 20 carbon atoms, such as a methyl group, an ethyl group, an n-propyl group, an i-propyl group, an n-butyl group, a sec-butyl group, an i-butyl group, a t-butyl group, an n-pentyl, an n-hexyl group, an n-heptyl group, a 2-ethylhexyl group, a heptyl group, an octyl group, a nonyl group, a decyl group, a cyclopropyl group, a cyclobutyl group, a cyclopentyl group, or a cyclohexyl group, and more preferably a linear, branched or cyclic alkyl group of 1 to 6 carbon atoms.

The aryl group is preferably a 6- to 14-membered monocyclic or polycyclic aryl group, for example, a phenyl group, a naphthyl group, an anthracenyl group, a phenanthrenyl group, a ferrocenyl group or the like.

The heteroaryl group is preferably a 5- to 14-membered monocyclic or polycyclic heteroaryl group having 1 to 4 atoms selected from nitrogen, oxygen and sulfur, for example, a thiophenyl group, a furyl group, a pyridyl group, a pyrrolyl group, a pyrrolinyl group, a pyrazinyl group, an oxazolyl group, a triazolyl group, a pyrimidyl group, a pyridazinyl group, a triazolyl group (for example, a 4H-1,2,4-triazolyl group, a 1H-1,2,3-triazolyl group, a 2H-1,2,3-triazolyl group or the like), a tetrazolyl group (for example, a 1H-tetrazolyl group, a 2H-tetrazolyl group or the like), an imidazolyl group, a pyrazolyl group, an indolyl group, an isoindolyl group, a benzothiophenyl group or the like.

The alkyl group, the aryl group, and the heteroaryl group may have a substituent as long as the effects of the present aspect are not adversely affected.

Also, the ring formed between ($R^1$ or $R^2$) and ($R^3$ or $R^4$), the ring formed between ($R^5$ or $R^6$) and ($R^7$ or $R^8$), the ring formed between ($R^3$ or $R^4$) and ($R^5$ or $R^6$), the ring formed between ($R^1$ or $R^2$) and $L^1$, or the ring formed between ($R^7$ or $R^8$) and $L^3$ may be any of alicycle, aromatic ring and hetero ring.

Examples of the alicycle include cyclopropane, cyclobutane, cyclopentane, cyclohexane, cycloheptane and the like.

Examples of the aromatic ring include benzene, naphthalene, anthracene, ferrocene and the like.

Examples of the hetero ring include thiophene, furan, pyran, pyridine, pyrrole, pyrazine, azepine, oxazole, triazole, pyrimidine, pyridazine, triazine, triazole, tetrazole, imidazole, pyrazole, morpholine, thiomorpholine, piperidine, piperazine, pyrrolidine, quinoline, isoquinoline, indole, isoindole, quinoxaline, phthalazine, quinolizine, quinazoline, quinoxaline, naphthyridine, benzofuran, benzothiophene, quinuclidine, tropane, phenothiazine and the like.

Examples of the group having an oxygen element include an oxy group, a carbonyl group, an alkoxy group (preferably, an alkoxy group of 1 to 10 carbon atoms), a phenoxy group and the like.

Examples of the group containing nitrogen include a tertiary amino group, a pyridyl group and the like.

Examples of the tertiary alkoxy group include a 1,1-dimethylethoxy group (=t-butoxy group), a 1,1-dimethylpropoxy group, a 1-methyl-1-ethylpropoxy group, a 1,1-diethylpropoxy group and the like.

Chemical Formula 7

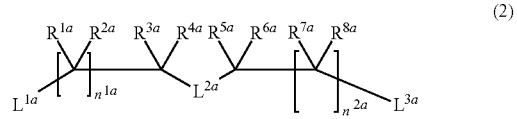

(2)

In formula (2),
$L^{2a}$ represents —O— or —N(—CH$_2$—R$^{11}$)—,
$R^{11}$ represents a hydrogen atom or a C1-6 alkyl group,
$L^{1a}$ represents —OR$^{12}$ or —N(R$^{13}$)R$^{14}$,
$L^{3a}$ represents —OR$^{121}$ or —N(R$^{131}$)R$^{141}$,
$R^{12}$ and $R^{121}$ each, independently, represents a C1-6 alkyl group,
$R^{13}$ and $R^{131}$ each, independently, represents a methyl group, an ethyl group, or an n-propyl group,
$R^{14}$ and $R^{141}$ each, independently, represents a C1-6 alkyl group (provided that when $L^{2a}$ is —O— and $L^{1a}$ is —OR$^{12}$, $L^{3a}$ is —N(R$^{121}$)R$^{141}$ and, when $L^{2a}$ is —O— and $L^{3a}$ is —OR$^{121}$, $L^{1a}$ is —N(R$^{13}$)R$^{14}$),
$n^{1a}$ and $n^{2a}$ each, independently, represents an integer of 1 to 3,
$R^{1a}$ to $R^{8a}$ each, independently, represents a hydrogen atom, a C1-6 alkyl group or phenyl group and may form a ring between ($R^{1a}$ or $R^{2a}$) and ($R^{3a}$ or $R^{4a}$), or may form a ring between ($R^{5a}$ or $R^{6a}$) and ($R^{7a}$ or $R^{8a}$).

Also, the ring formed between ($R^{1a}$ or $R^{2a}$) and ($R^{3a}$ or $R^{4a}$), or the ring formed between ($R^{5a}$ or $R^{6a}$) and ($R^{7a}$ or $R^{8a}$) may be any of an alicycle, an aromatic ring and a hetero ring.

Examples of the alicycle include cyclopropane, cyclobutane, cyclopentane, cyclohexane, cycloheptane and the like.

Examples of the aromatic ring include benzene, naphthalene, anthracene, ferrocene and the like.

Examples of the hetero ring include thiophene, furan, pyran, pyridine, pyrrole, pyrazine, azepine, oxazole, triazole, pyrimidine, pyridazine, triazine, triazole, tetrazole, imidazole, pyrazole, morpholine, thiomorpholine, piperidine, piperazine, pyrrolidine, quinoline, isoquinoline, indole, isoindole, quinoxaline, phthalazine, quinolizine, quinazoline, quinoxaline, naphthyridine, benzofuran, benzothiophene, quinuclidine, tropane, phenothiazine and the like.

Examples of suitable coordinating compound used in the present aspect include bis[2-(N,N-dimethylamino)ethyl] ether, 1-(2-(dimethylamino)ethoxy)-N,N,2-trimethylpropane-2-amine, 1,1'-oxybis(N,N,2-trimethylpropane-2-amine, 2-(2-(dimethylamino)ethoxy)-N,N-dimethylcyclohexaneamine, 2-(2-(dimethylamino)-2-methylpropoxy)-N,N-dimethylcyclohexaneamine, 2,2'-oxybis(N,N-dimethylcyclohexaneamine), 1,1'-oxybis(methylene)bis(N,N-dimethylcyclohexaneamine), 2,2'-oxybis(N,N-dimethyl-1,2-diphenylethaneamine), N,N'-(2,2'-oxybis(ethane-2,1-diyl))bis(N,2-dimethylpropane-1-amine), 1,1'-(tetrahydrofuran-2,5-diyl)bis(N,N-dimethylmethaneamine), 1,1'-(furan-2,5-diyl)bis(N,N-dimethylmethaneamine), N,N-dimethyl-2-((1-methylpyrrolidin-2-yl)methoxy)ethaneamine, 2,2'-oxybis(methylene)bis(1-methylpyrrolidine), 1,1'-(2,2'-oxybis(ethane-2,1-diyl))dipyrrolidine, 2-(2-methoxyphenoxy)-N,N-dimethylethaneamine, 2,2'-oxybis(N,N-dimethylaniline), N4,N4,N6,N6-tetramethyldibenzo[b,d]furan-4,6-diamine, 2,2'-thiobis(N,N-dimethylaniline), 2-(2-(dimethylamino)ethoxyl-N-(2-methoxyethyl)-N-methylethaneamine, 3,3'-oxybis(N,N,2,3-tetramethylbutane-amine), bis[2-(N,N-dimethylamino)-1-methylethyl]ether, bis[3-(N,N-dimethylamino)propyl]ether, bis[2-(N,N-diethylamino)ethyl]ether, bis[2-(N,N-diethylamino)-1-methylethyl]ether, bis(2-(N,N-diethylamino)propyl)ether, bis[2-(N,N-dimethylamino)-1-methylpropyl]ether, (2-dimethylaminoethyl-3-dimethylaminopropyl)ether, 3-(2-(dimethylamino)-2-methylpropoxy)-N,N,2,2-tetramethylpropane-1-amine, o-ethoxy-2-(N,N-dimethylamino)ethoxybenzene, 1-(2-methoxyphenoxy)-N,N,2-trimethylpropane-2-amine and the like. Among these compounds, bis[2-(N,N-dialkylamino)alkyl]ether, 2,2'-oxybis(N,N-dialkylcycloalkylamine), and 2-(2-(dialkylamino)alkoxy)-N,N-dialkylcycloalkylamine are preferable and bis[2-(N,N-dimethylamino)ethyl]ether, 1-(2-(dimethylamino)ethoxy)-N,N,2-trimethylpropane-2-amine, 1,1'-oxybis(N,N,2-trimethylpropane-2-amine, 2-(2-(dimethylamino)ethoxy)-N,N-dimethylcyclohexaneamine, 2,2'-oxybis(N,N-dimethylcyclohexaneamine), and (2-dimethylaminoethyl-3-dimethylaminopropyl)ether are particularly preferable.

Examples of another suitable coordinating compound used in the present aspect include N-(2-aminoethyl)-1,2-ethanediamine, pentamethyldiethylenetriamine, diamidinopyridine, 3,5-di(2-pyridyl)pyridine, 2,6-di(2-pyridyl)pyridine, N-methyl-di(N,N-2-methoxyethyl)amine, N,N-bis(2-methoxyethyl)butane-1-amine, 7-methyl-1,4,7-dioxazonane, 1,4,7-trimethyl-1,4,7-triazonane, 1,4,7-trimethyl-1,4,7-triazecane, N1-(2-(dimethylamino)-2-methylpropyl)-N1,N2,N2,2-tetramethylpropane-1,2-diamine, N2-(3-(dimethylamino)butane-2-yl)-N2,N3,N3-trimethylbutane-2,3-diamine, N1-(2-(dimethylamino)-1,2-diphenylethyl)-N1,N2,N2-trimethyl-1,2-diphenylethane-1,2-diamine, N2-(3-(dimethylamino)-2,3-dimethylbutane-2-yl)-N2,N3,N3,2,3-pentamethylbutane-2,3-diamine, 2,6-bis(2-methoxypropane-2-yl)pyridine, bis(2-t-butoxyethyl)ether, N1-(2-(dimethylamino)ethyl)-N1,N2,N2-trimethylethane-1,2-diamine and the like. Among these compounds, N,N-bis(2-methoxyethyl)butane-1-amine and N1-(2-(dimethylamino)ethyl)-N1,N2,N2-trimethylethane-1,2-diamine are particularly preferable.

Other examples of the coordinating compound used in the present aspect include 1,1,1-tris(dimethylaminomethyl)ethane, 1,1,1-tris(diphenylaminomethyl)ethane, tris(1-pyrazolyl)methane, tris(3,5-dimethyl-1-pyrazolyl)methane, tris(3,5-diisopropyl-1-pyrazolyl)methane, tris(3,5-diphenyl-1-pyrazolyl)methane, 1,1,1-tris(3,5-dimethyl-1-pyrazolyl)ethane, 1,1,1-tris(3,5-dimethyl-1-pyzolyl)propane, 1,1,1-tris(3,5-dimethyl-1-pyrazolyl)butane, tris(2-pyridyl)methane, tris(6-methyl-2-pyridyl)methane, tris(2-pyridyl)amine, tris(2-pyridyl)phosphine, tris(2-pyridyl)phosphine oxide, tris(2-pyridyl)hydroxymethane, tris(1-imidazolyl)methane, tris(3,5-dimethyl-1-pyrazolyl)methane, tris(3,5-diethyl-1-pyrazolyl)methane, tris(3,4,5-trimethyl-1-pyrazolyl)methane, tris(3,5-dimethyl-4-n-butyl-1-pyrazolyl)methane, tris(3-phenyl-5-methyl-1-pyrazolyl)methane, tris(3-(4-tolyl)-5-methyl-1-pyrazolyl)methane, tris(3-(4-anisyl)-5-methyl-1-pyrazolyl)methane, tris(3-(2-pyridyl)-5-methyl-1-pyrazolyl)methane, tris(3-(3-pyridyl)-5-methyl-1-pyrazolyl)methane, tris(3-(4-pyridyl)-5-methyl-1-pyrazolyl)methane, tris(3-phenyl-1-pyrazolyl)methane, 1-methyl-tris(3-phenyl-1-pyrazolyl)methane, methyl-tris(3-ethyl-1-pyrazolyl)methane, methyl-tris(3-phenyl-1-pyrazolyl)methane, methyl-tris(3,5-dimethyl-1-pyrazolyl)methane, tris(3-(4-tolyl)-1-pyrazolyl)methane, tris(3-(4-anisyl)-1-pyrazolyl)methane, tris(3-propyl-1-pyrazolyl)methane, tris(3-ethyl-1-pyrazolyl)methane, tris(3-methyl-1-pyrazolyl)methane, tris(3-t-butyl-1-pyrazolyl)methane, tris((2-dimethylamino)ethyl)amine, N,N',N'',N'''-hexamethyl-triethylenetetraamine; N,N'-bis(2-hydroxypropyl)piperazine, 1,8-diazabicyclo(5,4,0)undecene-7,1,4-bis(2-hydroxypropyl)-2-methylpiperazine, bis(N,N-diethylaminoethyl)adipate, 2-[N-(dimethylaminoethoxyethyl)-N-methylamino]ethanol; ethylenediaminetetraacetic acid; porphin, porphyrin, phthalocyanine and the like.

The coordinating compound is usually allowed to exist in a reaction system in an amount within a range from 0.01 mol % to a solvent amount, preferably from 1 to 500 mol %, more preferably from 50 to 200 mol %, and particularly preferably from 90 to 120 mol %, based on a lithium element in a lithiating agent.

The aromatic compound used in the present aspect is a compound having a ring which has (4n+2) (provided that n represents an integer) n electrons. Examples of the ring contained in the aromatic compound used in the present aspect include monocyclic or polycyclic 6- to 10-membered aromatic hydrocarbon rings, such as benzene, naphthalene, anthracene, and phenanthrene; and monocyclic or polycyclic 5- to 10-membered aromatic hetero ring having 1 to 4 atoms selected from nitrogen, oxygen and sulfur, such as thiophene, furan, pyran, pyridine, pyrrole, pyrazine, azepine, azocine, azonine, azecine, oxazole, thiazole, pyrimidine, pyridazine, triazine, triazole, tetrazole, imidazole, pyrazole, morpholine, thiomorpholine, piperidine, piperazine, quinoline, isoquinoline, indole, isoindole, quinoxaline, phthalazine, quinolizine, quinazoline, quinoxaline, naphthyridine, chromene, benzofuran, and benzothiophene. Among these rings, a monocyclic aromatic ring is preferable. That is, the aromatic compound used in the present aspect is preferably a monocyclic aromatic compound.

Also, the ring may further have a substituent. The substituent is not particularly limited and examples thereof include: halogen atoms such as fluorine, bromine, chlorine, and iodine; linear, branched or cyclic alkyl group of 1 to 20 carbon atoms (also including alkyl substituted with cycloalkyl), such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, cyclopropyl, cyclobutyl, cyclopentyl, cyclohexyl, cycloheptyl, cyclooctyl, cyclononyl, and cyclodecyl; linear, branched or cyclic alkenyl group of 2 to 20 carbon atoms, such as vinyl, allyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icocenyl, hexadienyl, and dodecatrienyl; linear, branched or cyclic alkynyl groups of 2 to 20 carbon atoms, such as ethynyl, butynyl, pentynyl, hexynyl, heptynyl, octynyl, nonynyl, cyclooctynyl, cyclononynyl, and cyclodecinyl; 5- to 10-membered monocyclic or bicyclic aryl groups such as phenyl, naphthyl, and anthranyl; alkoxy groups of 1 to 20 carbon atoms, such as methoxy, ethoxy, propoxy, butoxy, pentyloxy, hexyloxy, heptyloxy, octyloxy, nonyloxy, decyloxy, dodecyloxy, hexadecyloxy, and octadecyloxy; aryloxy groups such as phenoxy and naphthyloxy; alkylthio group of 1 to 20 carbon atoms, such as methylthio, ethylthio, propylthio, butylthio, pentylthio, hexylthio, heptylthio, octylthio, nonylthio, decylthio, dodecylthio, hexadecylthio, and octadecylthio; arylthio groups such as phenylthio and naphthylthio; substituted carbonyl groups such as acyl of 2 to 20 carbon atoms (e.g. acetyl, propanoyl, butanoyl, pentanoyl, hexanoyl, heptanoyl or the like), benzoyl, and naphthoyl; substituted oxycarbonyl groups such as methoxycarbonyl, ethoxycarbonyl, tert-butoxycarbonyl, n-decyloxycarbonyl, and phenoxycarbonyl; substituted carbonyloxy groups such as acyloxy of 2 to 20 carbon atoms (e.g. acetyloxy, propanoyloxy, butanoyloxy, pentanoyloxy, hexanoyloxy, heptanoyloxy or the like), benzoyloxy, and naphthoyloxy; substituted sulfonyl groups such as methylsulfonyl, ethylsulfonyl, propylsulfonyl, butylsulfonyl, pentylsulfonyl, hexylsulfonyl, heptylsulfonyl, octylsulfonyl, phenylsulfonyl, and naphthylsulfonyl; carbamoyl groups substituted with one to two groups selected from alkyl, alkenyl and aryl, such as N-methylcarbamoyl and N,N-diphenylcarbamoyl; sulfamoyl groups substituted with one to two groups selected from alkyl, alkenyl and aryl, such as N-phenylsulfamoyl and N,N-diethylcarbamoyl; substituted carbonylamino groups such as acylamino of 2 to 20 carbon atoms (e.g. acetylamino, tert-butylcarbonylamino, n-hexylcarbonylamino or the like), benzoylamino, and naphthoylamino; ureide groups substituted with one or two groups selected from alkyl, alkenyl and aryl, such as N-methylureide and N,N-diethylureide; substituted sulfonylamino groups such as sulfonylamino of 1 to 20 carbon atoms (e.g. methylsulfonylamino, tert-butylsulfonylamino, n-octylsulfonylamino or the like), phenylsulfonylamino, and naphthylsulfonylamino; monosubstituted or disubstituted amino groups such as methylamino, phenylamino, tert-butoxycarbonylamino, pivaloylamino, benzylamino, phthaloylamino, N,N-dimethylamino group, N,N-diethylamino group, N,N-diphenylamino group, and N-methyl-N-phenylamino group; nitro groups; cyano groups; substituted silyl groups such as trimethylsilyl and triethylsilyl; silyloxy groups such as t-butyldimethylsilyloxy group;
5- to 10-membered monocyclic or polycyclic hetero ring residues having one to fours atoms selected from nitrogen, oxygen and sulfur, such as thiophene, furan, pyran, pyridine, pyrrole, pyrazine, azepine, azocine, azonine, azecine, oxazole, thiazole, pyrimidine, pyridazine, triazine, triazole, tetrazole, imidazole, pyrazole, morpholine, thiomorpholine, piperidine, piperazine, quinoline, isoquinoline, indole, isoindole, quinoxaline, phthalazine, quinolizine, quinazoline, quinoxaline, naphthyridine, chromene, benzofuran, and benzothiophene; haloalkyloxy groups such as a difluoromethoxy group, a trifluoromethoxy group, a chlorodifluoromethoxy group, a bromodifluoromethoxy group, a 2-fluoroethoxy group, a 2-chloroethoxy group, a 2,2,2-trifluoroethoxy group, a 1,1,2,2-tetrafluoroethoxy group, a pentafluoroethoxy group, a 2,2,3,3-tetrafluoropropyloxy group, and a 1,1,2,3,3,3-hexafluoropropyloxy group; alkoxyhaloalkyloxy groups such as a methoxytetrafluoroethoxy group; haloalkoxyalkyloxy groups such as a trifluoromethoxyethoxy group; haloalkoxyhaloalkyloxy groups such as a trifluoromethoxytetrafluoroethoxy group; haloalkoxyalkyl groups such as a difluoro(methoxy)methyl group; haloalkoxyhaloalkyl groups such as a 2,2,2-trifluoro-1-methoxy-1-(trifluoromethyl) ethyl group; and all haloalkyl groups known in the electronic material field such as liquid crystals, pharmaceuticals, agricultural chemicals and the like, for example, a fluoromethyl group, a chloromethyl group, a bromomethyl group, an iodomethyl group, a difluoromethyl group, a chlorofluoromethyl group, a dichloromethyl group, a bromofluoromethyl group, a trifluoromethyl group, a chlorodifluoromethyl group, a dichlorofluoromethyl group, a trichloromethyl group, a bromodifluoromethyl group, a bromochlorofluoromethyl group, a dibromofluoromethyl group, a 2-fluoroethyl group, a 2-chloroethyl group, a 2-bromoethyl group, a 2,2-difluoroethyl group, a 2-chloro-2-fluoroethyl group, a 2,2-dichloroethyl group, a 2-bromo-2-fluoroethyl group, a 2,2,2-trifluoroethyl group, a 2-chloro-2,2-difluoroethyl group, a 2,2-dichloro-2-fluoroethyl group, a 2,2,2-trichloroethyl group, a 2-bromo-2,2-difluoroethyl group, a 2-bromo-2-chloro-2-fluoroethyl group, a 2-bromo-2,2-dichloroethyl group, a 1,1,2,2-tetrafluoroethyl group, a pentafluoroethyl group, a 1-chloro-1,2,2,2-tetrafluoroethyl group, a 2-chloro-1,1,2,2-tetrafluoroethyl group, a 1,2-dichloro-1,2,2-trifluoroethyl group, a 2-bromo-1,1,2,2-tetrafluoroethyl group, a 2-fluoropropyl group, a 2-chloropropyl group, a 2-bromopropyl group, a 2-chloro-2-fluoropropyl group, a 2,3-dichloropropyl group, a 2-bromo-3-fluoropropyl group, a 3-bromo-2-chloropropyl group, a 2,3-dibromopropyl group, a 3,3,3-trifluoropropyl group, a 3-bromo-3,3-difluoropropyl group, a 2,2,3,3-tetrafluoropropyl group, a 2-chloro-3,3,3-trifluoropropyl group, a 2,2,3,3,3-pentafluoropropyl group, a 1,1,2,3,3,3-hexafluoropropyl group, a heptafluoropropyl group, 2,3-dichloro-1,1,2,3,3-pentafluoropropyl group, a 2-fluoro-1-methylethyl group, a 2-chloro-1-methylethyl group, a 2-bromo-1-methylethyl group, 2,2,2-trifluoro-1-(trifluoromethyl)ethyl group, a 1,2,2,2-tetrafluoro-1-(trifluoromethyl)ethyl group, a 2-fluorobutyl group, 2-chlorobutyl group, a 2,2,3,3,4,4-hexafluorobutyl group, a 2,2,3,4,4,4-hexafluorobutyl group, a 2,2,3,3,4,4-hexafluorobutyl group, a 2,2,3,3,4,4,4-heptafluorobutyl group, a 1,1,2,2,3,3,4,4-octafluorobutyl group, a nonafluorobutyl group, a 4-chloro-1,1,2,2,3,3,4,4-octafluorobutyl group, a 2-fluoro-2-methylpropyl group, a 1,2,2,3,3,3-hexafluoro-1-(trifluoromethyl)propyl group, a 2-chloro-1,1-dimethylethyl group, a 2-bromo-1,1-dimethylethyl group, a 5-chloro-2,2,3,4,4,5,5-heptafluoropentyl group, a tridecafluorohexyl group and the like.

These substituents may further have a substituent. Further substituent is not particularly limited as long as it is not involved in the reaction. Examples of further substituent include lower alkyl groups such as methyl, ethyl, propyl, and butyl; aryl groups such as phenyl and naphthyl; and halogen atoms such as chlorine and fluorine. Further substituent preferably has a halogen atom and examples thereof include haloalkylhalobenzene which may have the other substituent and the like. Specific examples thereof include o-difluorobenzene, 3,4-difluoro-benzotrifluoride, 3,4-difluoro-nitrobenzene, 2,6-dibromo-pyridine and the like.

The aromatic compound used in the present aspect is preferably a halogenated aromatic compound which may have the other substituent, more preferably monofluorobenzene which may have the other substituent, difluorobenzene which may have the other substituent, trifluorobenzene which may have the other substituent, monochlorobenzene which may have the other substituent, dichlorobenzene which may have the other substituent, or trichlorobenzene which may have the other substituent, and particularly preferably trifluoromethylfluorobenzene or trifluoromethyldifluorobenzene.

The halogenated unsaturated aliphatic compound used in the present aspect is a halogen derivative of a hydrocarbon having a carbon-carbon double bond. The halogen is preferably attached to at least one of carbon elements constituting the carbon-carbon double bond. Examples thereof include vinyl halides such as vinyl bromide, vinyl chloride, and vinyl fluoride; 1-bromo-1-cyclohexene, 1-bromo-1-cyclooctene and the like.

The aromatic compound or halogenated unsaturated aliphatic compound is usually reacted in an amount within a range from 20 to 2,000 mol %, preferably from 20 to 500 mol %, more preferably from 50 to 200 mol %, and particularly preferably from 90 to 120 mol %, based on a lithium element in a lithiating agent.

The lithiating agent used in the present aspect is conventionally known. Examples thereof include lithium metals; alkyl lithiums such as methyl lithium, ethyl lithium, propyl lithium, butyl lithium, pentyl lithium, hexyl lithium, methoxymethyl lithium, and ethoxymethyl lithium; alkenyl lithiums such as vinyl lithium, propenyl lithium, and butenyl lithium; alkynyl lithiums such as ethynyl lithium, butynyl lithium, pentynyl lithium, and hexynyl lithium; aralkyl lithiums such as benzyl lithium and phenylethyl lithium; lithiumamides such as lithiumdiisopropylamide; and the like. Among these lithiating agents, alkyl lithium, alkenyl lithium, and alkynyl lithium are preferable, and methyl lithium, ethyl lithium, propyl lithium, n-butyl lithium, sec-butyl lithium, iso-butyl lithium, tert-butyl lithium, n-hexyl lithium, n-octyl lithium, n-decyl lithium, vinyl lithium, methoxymethyl lithium, benzyl lithium, phenyl lithium, 2-thienyl lithium, and tri(n-butyl)magnesium lithium are more preferable. From the viewpoint of ease of availability and operability, n-butyl lithium and methyl lithium are preferable, and n-butyl lithium is more preferable.

In the reaction of an aromatic compound or a halogenated unsaturated aliphatic compound with a lithiating agent in the present aspect, a solvent can be optionally used. Examples of the solvent include n-hexane, n-heptane, cyclohexane, methylcyclohexane, tetrahydrofuran, diethylether, diisopropylether, dibutylether, methyl-t-butyl ether, cyclopentyl methyl ether, dimethoxyethane, dioxane, toluene, xylene, mesitylene, chlorobenzene, N,N-dimethylformamide, 1,3-dimethyl-2-imidazolidinone, hexamethylphosphorictriamide, triethylamine, pyridine and the like, and tetrahydrofuran, n-hexane and toluene are used particularly preferably. These solvents can be used alone, or two or more kinds of these solvents can be used in combination.

The use amount of the solvent in the present aspect is from 100 liters to 0 liter, preferably from 10 liters to 0.001 liter, and more preferably from 5 liters to 0.01 liter, based on 1 mol of the aromatic compound or halogenated unsaturated aliphatic compound in the step of reacting the aromatic compound or halogenated unsaturated aliphatic compound with a lithiating agent.

Examples of the reaction by the lithiating agent in the present aspect include a lithiation reaction by deprotonation and a lithiation reaction by halogen-lithium substitution. In the present aspect, the aromatic compound and lithiating agent are preferably subjected to the lithiation reaction by deprotonation. Herein, "subjecting to the lithiation reaction by deprotonation" means that protons of the aromatic compound are extracted by an organolithium having a high basicity, such as n-butyl lithium or lithiumdiisopropylamide, lithiumamide or the like to produce an aromatic lithium compound in which proton and lithium are exchanged.

It was necessary that the reaction of the aromatic compound or halogenated unsaturated aliphatic compound with the lithiating agent in the prior art was carried out at very low temperature so as to prevent a decrease in yield of the organolithium compound. However, in the present aspect, the organolithium compound can be obtained in a high yield without adjusting to very low temperature. That is, the reaction of the aromatic compound or halogenated unsaturated aliphatic compound with the lithiating agent in the present aspect can be carried out under temperature conditions within a range from −40 to 40° C., preferably from −40° C. to 20° C., and more preferably from −20° C. to 10° C. The reaction can be carried out by a batch type reactor, a continuous batch type (cascade type) reactor, a continuous flow type reactor (including a microreactor) and the like.

Although details are unclear, it is considered that, in the liquid containing the organolithium compound produced by the reaction of the aromatic compound or halogenated unsaturated aliphatic compound with the lithiating agent in the present aspect, the coordinating compound containing three or more elements having a coordinating ability in a molecule, at least one thereof being a nitrogen element, or the coordinating compound containing three or more oxygen elements having a coordinating ability in a molecule, at least one of the groups containing the oxygen elements having a coordinating ability being a tertiary alkoxy group, allowed to exist at the time of the reaction, is chelate-coordinated with a lithium element in the organolithium compound. It is estimated that the organolithium compound can be obtained in a high yield even under mild conditions by the production method of the present aspect since the stability of the organolithium compound is specifically enhanced by chelate-coordinating of the coordinating compound with the organolithium compound, and thus decomposition, dimerization and oligomerization of the organolithium compound are suppressed.

Next, a method for producing a substituted aromatic compound according to the second aspect of the present invention will be described. With respect to the same matters as in the above first aspect, repetitive descriptions are omitted.

The method for producing a substituted aromatic compound of the present aspect includes the steps of reacting an aromatic compound with a lithiating agent in the presence of a coordinating compound containing three or more elements having a coordinating ability in a molecule, at least one thereof being a nitrogen element, or a coordinating compound containing three or more oxygen elements having a coordinating ability in a molecule, at least one of the groups containing the oxygen elements having a coordinating ability being a tertiary alkoxy group, at a temperature of 40° C. or lower (preferably from −60 to 40° C., and more preferably from −40 to 40° C.) to obtain an organolithium compound, and reacting the organolithium compound obtained in the above step with an electrophilic compound at a temperature of −40° C. to 40° C.

The coordinating compound is preferably a compound represented by formula (1) or (2).

It is possible to use, as the aromatic compound, those described in the first aspect, and monocylic aromatic compounds are preferable.

It is possible to respectively use, as the lithiating agent, those described in the first aspect.

The aromatic compound and lithiating agent are preferably subjected to a lithiation reaction by deprotonation.

In the step of obtaining the organolithium compound, a solvent can be optionally used in the reaction of the aromatic compound with the lithiating agent. It is possible to respectively use, as the solvent, those described in the first aspect in the use amount similar to the use amount described in the first aspect.

The electrophilic compound used in the present aspect is not particularly limited as long as it is a compound having a functional group which has an electron-accepting ability (i.e. a compound capable of reacting as an electrophile), and is preferably a compound which is reacted with a functional group having a large electron density and an unshared electron pair. The relevant compound contains all electrophilic compounds used in the halogen-metal exchange reaction using a known organolithium reagent and the lithiation reaction by deprotonation.

Examples of the electrophilic compound used in the present aspect include halogens such as chlorine, bromine, and iodine; inorganic substances such as solid-state sulfur, sulfur dioxide, and oxygen; carbon dixoide; sulfonic acids such as a trifluoromethylsulfonic acid methyl ester and a trifluoromethylbenzenesulfonic acid; dimethylsulfuric acid; nitriles such as acetonitrile, propionitrile, and benzonitrile; imines such as benzophenoneimine and acetophenoneimine; halogenated silicones such as chlorotrimethylsilane, chlorodimethylphenylsilane, chlorodimethylsilane, and bromotrimethylsilane; chlorosilane compounds such as chlorodialkylhydrosilane; halogenated borons such as trichloroborane and tribromoborane; boronic acid esters such as a pinacolboronic acid ester, a trimethylboronic acid ester, and a triisopropylboronic acid ester; boron compounds such as tris(isopropoxy)borane, methoxydiethylborane, tris(dimethylamino)borane, and bis(pinacolate)diborane; tin compounds such as dibutyltin dichloride and diphenyltin dibromide; aldehydes such as paraformaldehyde, acetoaldehyde, propionaldehyde, butylaldehyde, acrylaldehyde, benzaldehyde, and nicotinaldehyde; ketones such as acetone, 2-butanone, benzophenone, acetophenone, and tert-butyl-4-oxo-1-piperidine carboxylate; formamides such as N,N-methylphenylformamide and N,N-dimethylformamide; orthoesters such as ethyl orthoformate and methyl orthoformate;
methyl formate, trimethyl phosphite, N-formylmorpholine, and N-formylpiperidine; esters such as trifluoroethyl acetate, ethyl chloroformate, phenyl chloroformate, methyl formate, ethyl formate, ethyl acetate, butyl acetate, octyl acetate, phenyl acetate, methyl benzoate, ethyl benzoate, and phenyl benzoate; acid anhydrides such as acetic anhydride, phthalic anhydride, succinic anhydride, and maleic anhydride; halogenated acyls such as acetyl chloride, benzoyl chloride, and 2-pyridinecarbonyl chloride; oxiranes such as oxirane and 2-methyl-oxirane; aziridines such as 6-azabicyclo[3,1,0]hexane and 7-azabicyclo[4,1,0]heptane; α,β-unsaturated ketones such as 3-oxo-1,3-diphenyl-1-propene and 2-methyl-3-oxo-3-diphenyl-1-propene; halogenated alkyls such as methyl iodide, ethyl iodide, butyl iodide, methyl bromide, ethyl bromide, hexyl bromide, octyl bromide, 1,2-diiodoethane, 1,2-dibromoethane, 1,6-diiodohexane, 1,8-dibromooctane, and 1,2-dibromocyclopentene; acid imides such as N-bromosuccinic acid imide, N-iodosuccinic acid imide, N-chlorosuccinic acid imide, and N-bromophthalic acid imide; disulfides such as dimethyl disulfide and diphenyl disulfide; phosphines such as chlorodiphenylphosphine and chlorodimethylphosphine; phosphine oxides such as chlorodiphenylphosphine oxide and chlorodimethylphosphine oxide; heavy water and water; lactones such as γ-butyrolactone; 4-membered ring compounds such as oxetane; thioesters; phosgene-like compounds such as phosgene and triphosgene; thiophosgene; haloformic acid esters such as chloromethyl formate; halogenated benzyls such as benzyl chloride; hetero-cumulenes (e.g. butyl isocyanate, butyl isothiocyanate and the like) such as isocyanate and isothiocyanate; nitroso compounds; magnesium compounds (e.g. magnesium chloride and the like); calcium compounds (e.g. calcium chloride and the like); barium compound (e.g. barium chloride and the like); aluminum compounds (e.g. aluminum chloride, diethylaluminum chloride, tributylaluminum and the like); titanium compounds (e.g. titanium chloride, triisopropoxychlorotitanium and the like); zinc compounds (e.g. zinc chloride, zinc iodide, triethylaluminum and the like); manganese compounds (e.g. manganese chloride and the like); copper compounds (e.g. copper chloride, copper iodide, copper cyanate and the like); iron compounds (e.g. iron chloride and the like); transition metal compounds such as palladium and ruthenium (e.g. palladium chloride, rhodium chloride, iridium chloride, nickel chloride, cobalt chloride, tungsten chloride, molybdenum chloride, vanadium chloride and the like); and the like.

A solvent can be optionally used in the reaction of the organolithium compound with the electrophilic compound in the present aspect. Examples of the solvent include n-hexane, n-heptane, cyclohexane, methylcyclohexane, tetrahydrofuran, diethylether, diisopropylether, dibutylether, methyl-t-butylether, cyclopentyl methyl ether, dimethoxyethane, dioxane, toluene, xylene, mesitylene, chlorobenzene, N,N-dimethylformamide, 1,3-dimethyl-2-imidazolidinone, hexamethylphosphoric triamide, triethylamine, pyridine and the like. These solvents may be used alone, or two or more kinds of these solvents can be used in combination. Among these solvents, a polar solvent is preferable from the viewpoint of satisfactory balance between stability and reactivity, and tetrahydrofuran is particularly preferable.

The use amount of the solvent in the step of reacting the organolithium compound with the electrophilic compound is preferably from 100 liters to 0 liter, more preferably from 10 liters to 0.001 liter, and still preferably from 5 liters to 0.01 liter, based on 1 mol of the organolithium compound.

It was necessary that reaction of the organolithium compound with the electrophilic compound in the prior art was carried out at very low temperature so as to prevent a decrease in yield. However, in the present aspect, the substituted aromatic compound can be obtained in a high yield without adjusting to very low temperature. The reaction of the organolithium compound with the electrophilic compound in the present aspect can be carried out under temperature conditions within a range from −40 to 40° C., preferably from −40° C. to 20° C., and more preferably from −20° C. to 10° C. The reaction can be carried out by a batch type reactor, a continuous batch type (cascade type) reactor, a continuous flow type reactor (including a microreactor) and the like.

The reaction of the organolithium compound with the electrophilic compound in the present aspect is preferably carried out by maintaining a state where the electrophilic compound is more excessive than the organolithium compound. Herein, the "excess state" means that the organolithium compound synthesized separately is brought into contact with a large amount of the electrophilic compound little by little. Specifically, it is preferred to react by dropping a solution containing an organolithium compound in a solution containing an electrophilic compound. There is no particularly limitation on the dropping rate. However, the dropping rate is preferably controlled so that the organolithium compound dropped is not reacted with the solvent, not dimerized or oligomerized, or the organolithium compound is not further reacted with the produced substituted aromatic compound, and more preferably controlled so that the organolithium compound is completely consumed by contact with the electrophilic compound within a short time. In case the above lithiation reaction and this electrophilic reaction by dropping are continuously carried out, it is preferred that the amount required for dropping in the electrophilic reaction of the organolithium compound is sequentially obtained by the lithiation reaction using a continuous tubular flow type reactor or the like and the obtained organolithium compound is immediately subjected to the electrophilic reaction without being accumulated as possible (see, for example, Example 4)

Although details are unclear, it is estimated that the substituted aromatic compound can be obtained in a high yield even under mild conditions by the production method of the present aspect since the stability of the organolithium compound is enhanced by chelate-coordinating of the coordinating compound specified in the present aspect with the organolithium compound, and thus decomposition, dimerization and oligomerization of the organolithium compound are suppressed, resulting in an increase of the amount of the organolithium compound to be reacted with the electrophilic compound.

Next, the third aspect of the present invention will be described. With respect to the same matters as in the above first or second aspect, repetitive descriptions are omitted.

The third aspect of the present invention is use of a coordinating compound containing three or more elements having a coordinating ability in a molecule, at least one thereof being a nitrogen element, or a coordinating compound containing three or more oxygen elements having a coordinating ability in a molecule, at least one of the groups containing the oxygen elements having a coordinating ability being a tertiary alkoxy group, in a continuous flow type reactor, as an occlusion-preventing agent or a residence time extending agent in the production of an organolithium compound, or the production of a substituted aromatic compound by a reaction of an organolithium compound with an electrophilic compound.

The coordinating compound is preferably a compound represented by formula (1) or (2).

The organolithium compound is preferably produced based on the first aspect.

The substituted aromatic compound is preferably produced based on the second aspect.

The "continuous flow type reactor" means a general device in which a reagent is continuously introduced into a tubular reactor and a desired reaction is allowed to arise during which the reagent passes through the reactor, and then the reactant is continuously taken out from the tubular reactor and includes, for example, a microreactor, a flow reactor and the like.

The "occlusion-preventing agent" means an additive used to prevent non-smooth flow of a reagent through a tube as a result of occlusion caused by adhesion and accumulation of a by-product, an oligomer, a polymer and a slurry having a high viscosity to a continuous flow type reactor through which the reagent is passed, a transfer tube for connecting reaction vessels and the like.

The "residence time extending agent" means an additive used to prevent adverse influences such as occlusion of a tube, an increase in viscosity of a reagent, which obstruct flow of the reagent to be transferred, in the case of prolonging the residence time of the reagent in a continuous flow type reactor, a transfer tube and the like, or reopening flow of the reagent after stopping transfer for a long time.

Next, the fourth aspect of the present invention will be described. With respect to the same matters as in the above first to third aspects, repetitive descriptions are omitted.

The fourth aspect of the present invention is use of a coordinating compound containing three or more elements having a coordinating ability in a molecule, at least one thereof being a nitrogen element, or a coordinating compound containing three or more oxygen elements having a coordinating ability in a molecule, at least one of the groups containing the oxygen elements having a coordinating ability being a tertiary alkoxy group, as a reaction runaway inhibitor or a scaling inhibitor in the production of an organolithium compound, or the production of a substituted aromatic compound by a reaction of an organolithium compound with an electrophilic compound.

The "reaction runaway inhibitor" means an additive used to control an exothermic reaction by suppressing an increase in a reaction rate of a reagent, thereby suppressing foaming, boiling and the like, and inhibiting an adverse influence such as deterioration of quality of a product due to runaway of a reaction.

The "scaling inhibitor" means an additive used to inhibit adverse influences such as decrease in stirring efficiency and heat transfer efficiency, deterioration of cleaning operability, quality deterioration of the product as a result of adhesion of a reagent to a vessel caused by oligomerization, polymerization, insolubilization and the like in the batch type reaction vessel and the like.

Next, a ligand according to the fifth aspect of the present invention will be described. With respect to the same matters as in the above first or second aspect, repetitive descriptions are omitted.

The ligand of the present aspect is represented by the following formula (3):

Chemical Formula 8

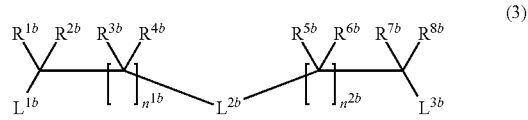

(3)

wherein, in formula (3),
$L^{2b}$ represents —O— or —N(—CH$_2$—R$^{21}$)—,
$R^{21}$ represents a hydrogen atom or a C1-6 alkyl group,
$L^{1b}$ represents —OR$^{22}$ or —N(R$^{23}$)R$^{24}$, $L^{3b}$ represents —OR$^{221}$ or —N(R$^{231}$)R$^{241}$,
$R^{22}$ and $R^{221}$ each, independently, represents a C1-6 alkyl group,
$R^{23}$ and $R^{231}$ each, independently, represents a methyl group, an ethyl group, or an n-propyl group,
$R^{24}$ and $R^{241}$ each, independently, represents a C1-6 alkyl group (provided that when $L^{2b}$ is —O— and $L^{1b}$ is —OR$^{22}$, $L^{3b}$ is —N(R$^{231}$)R$^{241}$ and, when $L^{2b}$ is —O— and $L^{3b}$ is —OR$^{221}$, $L^{1b}$ is —N(R$^{23}$)R$^{24}$),
$n^{1b}$ and $n^{2b}$ each, independently, represents an integer of 1 to 3,
$R^{1b}$ and $R^{2b}$ represent a C1-6 alkyl group,
$R^{3b}$ to $R^{8b}$ each, independently, represents a hydrogen atom or C1-6 alkyl group (provided that when $L^{2b}$ is —N—CH$_3$, $L^{1b}$ and $L^{3b}$ is —N(CH$_3$)CH$_3$ and $n^{1b}$ and $n^{2b}$ are 1, $R^{1b}$ to $R^{8b}$ are not simultaneously methyl groups) and
may form a ring between ($R^{1b}$ or $R^{2b}$) and ($R^{3b}$ or $R^{4b}$) or may form a ring between ($R^{5b}$ or $R^{6b}$) and ($R^{7b}$ or $R^{8b}$).

The ring formed between ($R^{1b}$ or $R^{2b}$) and ($R^{3b}$ or $R^{4b}$), or ring formed between ($R^{5b}$ or $R^{6b}$) and ($R^{7b}$ or $R^{8b}$) can be an alicycle, an aromatic ring, or a hetero ring.

EXAMPLES

The present invention will be specifically described by way of Examples and Comparative Examples, but the present invention is not limited to these Examples.

Examples 1 to 2 and Comparative Examples 1 to 6

Test Method A

Under a nitrogen atmosphere, 30 mL of tetrahydrofuran (containing 6 g of o-xylene as an internal standard), 35.0 mmol of a coordinating compound shown in Table 1 (a coordinating compound is not used in Comparative Example 1) and 6.06 g (33.3 mmol) of 3,4-difluoro-benzotrifluoride were charged in a reaction vessel equipped with a dropping funnel and a stirrer and then cooled to −50° C. After adding dropwise 15.1 g (35.0 mmol) of n-butyl lithium (1.6 mol/L hexane solution) at −50° C., the mixture was stirred at the same temperature for 1 hour to obtain a solution containing 2,3-difluoro-6-trifluoromethyl-phenyl lithium.

Next, this solution was heated to 0° C. and then stirred at the same temperature for 5 hours. A small amount of a sample was extracted from the solution and dissolved in methanol. By dissolution in methanol, 2,3-difluoro-6-trifluoromethyl-phenyl lithium was protonated to obtain a product containing 3,4-difluoro-benzotrifluoride (DFBT) as a main component. Using high-performance liquid chromatography (hereinafter abbreviated to HPLC), the production amount (%) of DFBT was quantitatively analyzed. The results are shown in Table 1.

Furthermore, the solution was left to stand at −15° C. for the time shown in Table 1. Then, the residual amount (%) of 3,4-difluoro-benzotrifluoride (DFBT) was quantitatively analyzed in the same manner as in above. The results are shown in Table 1.

TABLE 1

| | Amount of DFBT (%) | |
|---|---|---|
| Coordinating compound | After stirring at 0° C. for 5 hours | After leaving to stand at −15° C. (Standing time is shown in parentheses.) |
| Example 1: Me₂N–O–NMe₂ | 94 | 82 (32 hours) |
| Example 2: Me₂N–N(Me)–NMe₂ | 96 | 89 (22 hours) |
| Comparative Example 1: — | 84 | 25 (18 hours) |
| Comparative Example 2: Me₂N–NMe₂ | 87 | 29 (22 hours) |
| Comparative Example 3: i-Pr₂NH | 65 | 27 (22 hours) |
| Comparative Example 4: MeO–O–OMe | 61 | — |
| Comparative Example 5: (crown ether with O,O,O,O and Me,Me) | 46 | — |
| Comparative Example 6: Me₂N–OEt | 60 | — |

As is apparent from a comparison between Examples 1 to 2 and Comparative Examples 1 to 6, in the case of using a coordinating compound containing three or more elements having a coordinating ability in a molecule, at least one thereof being a nitrogen element, the amount of denaturation into a by-product such as an oligomer is suppressed when compared with the case of using the other coordinating compounds. This reveals that the coordinating compound containing three or more elements having a coordinating ability in a molecule, at least one thereof being a nitrogen element, considerably improve the stability of a lithiated compound even under mild conditions (0° C., −15° C.).

Example 3

Under a nitrogen atmosphere, 1.60 g (10 mmol) of bis[2-(N,N-dimethylamino)ethyl]ether was dissolved by adding to 2 mL of hexane. After cooling to −15° C., 6.25 mL (10 mmol) of n-butyl lithium (1.6 mol/L hexane solution) was added dropwise while maintaining at −15° C. to −5° C., followed by stirring for 15 minutes. To this mixture, 820 mg (5 mmol) of 4-fluoro-benzotrifluoride was added dropwise while maintaining at −15° C. to −5° C. After completion of the dropwise addition, the mixture was reacted at −15° C. for 1.5 hours to obtain a solution containing 2-fluoro-(5-trifluoromethyl)-phenyl lithium.

To this solution, 1.56 g (15 mmol) of trimethoxyborane was added dropwise at −15° C. to −10° C. After completion of the dropwise addition, this reaction solution was heated to room temperature and 10 mL of 1 mol/L hydrochloric acid was added thereto. After extraction with ethyl acetate, the organic layer was washed with saturated saline and dried over magnesium sulfate. The residue was filtered and concentrated to obtain 1-fluoro-(4-trifluoromethyl)phenylboronic acid in a yield of 69%.

Chemical Formula 9

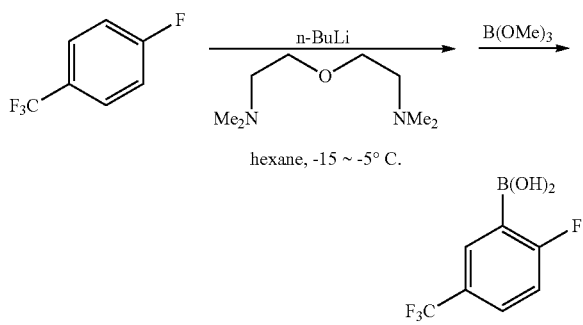

Comparative Example 7

In the same manner as in Example 3, except that bis[2-(N,N-dimethylamino)ethyl]ether was replaced by tetrahydrofuran, an attempt was made to carry out a reaction. As a result, the reaction solution caused color change into brown. After 30 minutes have passed since the initiation of the reaction, HPLC analysis was carried out. As a result, a large amount of by-product, which cannot be identified, was produced and only 43% of 4-fluoro-benzotrifluoride existed, and thus an isolation operation was abandoned.

As is apparent from a comparison between Example 3 and Comparative Example 7, use of bis[2-(N,N-dimethylamino)ethyl]ether enables lithiation and introduction of an electrophile under mild conditions at a temperature which is not very low temperature. It is considered that the yield can highly maintained even under mild reaction conditions (−15° C.) like Example 3 since the stability of a lithiated compound such as 2-fluoro-(5-trifluoromethyl)-phenyl lithium produced by lithiation of bis[2-(N,N-dimethylamino)ethyl]ether is improved. Accordingly, it is considered that the coordinating compound capable of improving the stability of the lithiated compound shown in Examples 1 and 2, i.e. a coordinating compound containing three or more elements having a coordinating ability in a molecule, at least one thereof being a nitrogen element, or a coordinating compound containing three or more oxygen elements having a coordinating ability in a molecule, at least one of the groups containing the oxygen elements having a coordinating ability being a tertiary alkoxy group, enables lithiation and introduction of a electrophile under mild conditions at a temperature which is not very low temperature.

Example 4

In a 1.0 mmφ tubular flow type reactor A adjusted at a temperature of −4° C., a tetrahydrofuran solution of 3,4-difluoro-benzotrifluoride having the concentration of 1.76 mol/L and bis[2-(N,N-dimethylamino)ethyl]ether having the concentration of 1.60 mol/L, and n-butyl lithium having the concentration of 1.6 mol/L were continuously fed through an inlet (an inner diameter of a mixing portion: 3.6 mm) of the reactor A in a mixing volume ratio of 1:1 so that the residence time becomes 6.6 minutes. After the reaction, a solution containing 2,3-difluoro-6-trifluoromethyl-benzene lithium was continuously taken out through an outlet of the reactor A.

On the other hand, a solution prepared by dissolving 6.01 g (100 mmol) of methyl formate in 5 mL of tetrahydrofuran and adjusting the temperature to −8° C. is charged in a reactor B. The above solution containing 2,3-difluoro-6-trifluoromethyl-phenyl lithium at −4° C. was taken out from the reactor A and then immediately added dropwise in the reactor B at a rate of 0.1 mL per 1 minute.

This operation was continued for 4 hours. The reaction could be continuously carried out for 4 hours without causing troubles such as clogging in the tubular flow type reactor A.

In the reactor B, stirring was carried out for 30 minutes after completion of the dropwise addition to obtain a solution containing 2,3-difluoro-6-trifluoromethylbenzaldehyde. A ratio of conversion into 2,3-difluoro-6-trifluoromethylbenzaldehyde from 3,4-difluoro-benzotrifluoride was 82%.

To the solution obtained in the reactor B, 20 mL of ethanol and 2.28 g (32.8 mmol) hydroxylamine hydrochloride were added and the mixture was refluxed for 1.5 hours. After completion of the reflux, the reaction solution was filtered and concentrated to obtain a crude crystal of 2,3-difluoro-6-trifluoromethyl-benz aldoxime as the objective product. This crude crystal was analyzed by HPLC and, as a result, the crude crystal showed a yield of 77% and a purity of 97% based upon the converted raw material.

Comparative Example 8

The same operation as in Example 4 was carried out, except that bis[2-(N,N-dimethylamino)ethyl]ether was not used. After 1.6 hours have passed since the initiation of the operation, the tubular flow type reactor A caused occlusion and the reaction had to be stopped. Although detailed cause of occlusion is unclear, it is considered that an oligomer or the like was produced because of low stability of 2,3-difluoro-6-trifluoromethyl-benzene lithium.

As is apparent from the above results, even when the aromatic compound or halogenated unsaturated aliphatic compound is reacted with the lithiating agent under comparatively mild conditions in the presence of a coordinating compound containing three or more elements having a coordinating ability in a molecule, at least one thereof being a nitrogen element, or a coordinating compound containing three or more oxygen elements having a coordinating ability in a molecule, at least one of the groups containing the oxygen elements having a coordinating ability being a tertiary alkoxy group, the organolithium compound can be obtained in a high yield. It is also found that the substituted aromatic compound can be obtained in a high yield even when the reaction of the organolithium compound obtained in the above method with the electrophilic compound is carried out under comparatively mild conditions.

According to a conventional manner, when the reaction of the aromatic compound with the lithiating agent is carried out by a tubular flow type reactor, the reactor causes occlusion and thus the reaction cannot be continued (Comparative Example 8). However, when the reaction of the aromatic compound with the lithiating agent is carried out by a tubular flow type reactor in the presence of a coordinating compound containing three or more elements having a coordinating ability in a molecule, at least one thereof being a nitrogen element, or a coordinating compound containing three or more oxygen elements having a coordinating ability in a molecule, at least one of the groups containing the oxygen elements having a coordinating ability being a tertiary alkoxy group, the reactor is less likely to cause occlusion, and thus the reaction can be efficiently carried out continuously for a long time (Example 4).

As described above, a coordinating compound containing three or more elements having a coordinating ability in a molecule, at least one thereof being a nitrogen element, or a coordinating compound containing three or more oxygen elements having a coordinating ability in a molecule, at least one of the groups containing the oxygen elements having a coordinating ability being a tertiary alkoxy group, can be used as an occlusion-preventing agent for a piping or the like, a residence time extending agent in a continuous flow type reactor, or a reaction runaway inhibitor or a scaling inhibitor, in the production of the organolithium compound, or the production of the substituted aromatic compound by the reaction of the organolithium compound with the electrophilic compound.

Examples 5 to 6 and Comparative Examples 9 to 14

Test Method B

Under a nitrogen atmosphere, 30 mL of tetrahydrofuran (containing 6 g of o-xylene as an internal standard), 35.0 mmol of a coordinating compound shown in Table 2 (a coordinating compound is not used in Comparative Example 9) and 6.06 g (33.3 mmol) of 3,4-difluoro-benzotrifluoride were charged in a reaction vessel equipped with a dropping funnel and a stirrer and then cooled to −50° C. After adding dropwise 15.1 g (35.0 mmol) of n-butyl lithium (1.6 mol/L hexane solution) at −50° C., the mixture was stirred at the same temperature for 1 hour to obtain a solution containing 2,3-difluoro-6-trifluoromethyl-phenyl lithium. A small amount of a sample was extracted from the solution at −50° C. and was added to a tetrahydrofuran/hexane solution of iodide (excess amount), prepared separately.

By the addition to the iodine solution, 2,3-difluoro-6-trifluoromethyl-phenyl lithium (LDFBT) was iodized to obtain a product containing 2-iodo-3,4-difluoro-benzotrifluoride (IDFBT) as a main component. The production amount (%) of IDFBT was quantitatively analyzed by HPLC.

Next, this solution was heated to 0° C. and stirred at the same temperature for 4 hours. Thereafter, the residual amount (%) of IDFBT was quantitatively analyzed in the same manner as in above. Furthermore, the solution was left to stand at −15° C. for the time shown in Table 2. Then, the residual amount (%) of IDFBT was quantitatively analyzed in the same manner as in above.

From the above analytical results, the residual amount (%) of 2,3-difluoro-6-trifluoromethyl-phenyl lithium (LDFBT) was calculated by the following equation.

"Residual amount (%) of LDFBT="residual amount (%) of IDFBT after a predetermined time has passed since temperature rise"/"production amount (%) of IDFBT at −50° C.]×100

The results are shown in Table 2.

TABLE 2

| | | Residual amount of LDFBT (%) | |
|---|---|---|---|
| | Coordinating compound | After stirring at 0° C. for 4 hours | After leaving to stand at −15° C. (Standing time is shown in parentheses.) |
| Example 5 | Me$_2$N∼O∼NMe$_2$ | 87 | 53 (32 hours) |
| Example 6 | Me$_2$N∼N(Me)∼NMe$_2$ | 91 | 61 (22 hours) |
| Comparative Example 9 | None | 84 | 9 (18 hours) |
| Comparative Example 10 | Me$_2$N∼NMe$_2$ | 77 | 3 (22 hours) |
| Comparative Example 11 | i-Pr$_2$NH | 57 | 0 (22 hours) |
| Comparative Example 12 | MeO∼O∼OMe | 60 | — |
| Comparative Example 13 | 12-crown-4 type (OMe, O, O, MeO) | 18 | — |
| Comparative Example 14 | Me$_2$N∼OEt | 30 | — |

Examples 7 to 10

In the same manner as in Test Method B, except that the solution after quantitative analysis of the amount (%) of IDFBT produced was heated to 0° C. and stirred at the same temperature for 4 hours, and also the solution was left to stand at 0° C. for the time shown in Table 3, a reaction was carried out. The results are shown in Table 3.

TABLE 3

| | Coordinating compound | Residual amount of LDFBT (%) | |
|---|---|---|---|
| | | After stirring at 0° C. for 4 hours | After leaving to stand at 0° C. (Standing time is shown in parentheses.) |
| Example 7 | Me₂N~~O~~NMe₂ | 94 | 45 (28 hours) |
| Example 8 | (NMe₂)(NMe₂)–O–NMe₂ | 82 | 33 (28 hours) |
| Example 9 | Me₂N–C(Me)(Me)–O–NMe₂ | 89 | 68 (28 hours) |
| Example 10 | MeO–CH₂CH₂–N(Bu)–CH₂CH₂–OMe | 80 | 23 (28 hours) |

Examples 11 to 13 and Comparative Examples 15

In the same manner as in Test Method B, except that the solution after quantitative analysis of the amount (%) of IDFBT produced was heated to 20° C. and stirred at the same temperature for 1 hours, and also the solution was left to stand at 20° C. for the time shown in Table 4, a reaction was carried out. The results are shown in Table 4.

TABLE 4

| | Coordinating compound | Residual amount of LDFBT (%) | |
|---|---|---|---|
| | | After stirring at 20° C. for 1 hour | After leaving to stand at 20° C. (Standing time is shown in parentheses.) |
| Example 11 | Me₂N~~O~~NMe₂ | 63 | 21 (4 hours) |
| Example 12 | Me₂N–C(Me)(Me)–O–C(Me)(Me)–NMe₂ | 81 | 36 (4 hours) |
| Example 13 | cyclohexyl(Me₂N)(O–CH₂CH₂–NMe₂) | 59 | 48 (4 hours) |
| Comparative Example 15 | Me₂N~~NMe₂ | 24 | 0 (4 hours) |

Example 14

In the same manner as in Test Method B, except that the reaction was carried out in a hexane solvent, a reaction was carried out. The results are shown in Table 5.

TABLE 5

| | Residual amount of LDFBT (%) | |
|---|---|---|
| Coordinating compound | After stirring at 0° C. for 4 hours | After leaving to stand at 15° C. (Standing time is shown in parentheses.) |
| Example 14 Me$_2$N$\frown$O$\frown$NMe$_2$ | 94 | 80 (22 hours) |

As is apparent form a comparison between Example 5 and Example 14, the lithiated compound can be stably kept not only in an aprotic polar solvent such as tetrahydrofuran, but also in a non-polar solvent such as hexane.

Example 15

Under a nitrogen atmosphere, 3,4-difluoro-benzotrifluoride (DFBT) (6.06 g, 33.3 mmol) and bis[2-(N,N-dimethylamino)ethyl]ether (5.87 g, 36.6 mmol) were dissolved in 30 mL of tetrahydrofuran in a 100 mL round-bottom flask (reactor A) made of glass equipped with a stirrer tip and a thermometer. After cooling to 10° C., n-butyl lithium (1.6 mol/L hexane solution) (21.9 mL, 14.5 g, 35.0 mmol) was added dropwise over 34 minutes while maintaining at 8 to 10° C., followed by stirring for 60 minutes.

On the other hand, a solution prepared by dissolving iodine (16.8 g, 66.2 mmol) and o-xylene (internal standard, 6.01 g) in tetrahydrofuran (60 mL, 53.2 g) and adjusting a temperature to −15° C. is charged in a reactor B. The entire amount of the solution containing 2,3-difluoro-6-trifluoromethyl-phenyl lithium (LDFBT) at 10° C. was taken out from the reactor A and then immediately added dropwise over 50 minutes while maintaining the inner temperature of the reactor B at −13 to −17° C., followed by further stirring in the same temperature range for 10 minutes. This reaction solution was quantitatively analyzed by HPLC and, as a result, the objective 2-iodo-3,4-difluoro-benzotrifluoride (IDFBT) showed a yield of 74%.

$^1$H-NMR (CDC$_3$)

7.27 ppm (q, J=8.3 Hz, 1H), 7.48 (ddd, J=8.9, 4.8, 1.7 Hz, 1H) Boiling point: 49-55° C./7 mmHg

Comparative Example 16

In the same manner as in Example 15, except that bis[2-(N,N-dimethylamino)ethyl] ether was not added, a reaction was carried out. After the reaction, quantitative analysis was carried out by HPLC and, as a result, the objective 2-iodo-3, 4-difluoro-benzotrifluoride (IDFBT) showed a yield of 1.4%.

Example 16

Production of 1-[2-(dimethylamino)ethoxy]-N,N,2-trimethylpropane-2-amine

To toluene (100 ml), sodium hydroxide (16.7 g, 418 mmol) and 2-dimethylamino-2-methyl-1-propanol (23.4 g, 200 mmol) were added and the mixture was heated at reflux for 2 hours. After cooling to 70° C., β-dimethylaminoethyl chloride hydrochloride (28.8 g, 200 mmol) was added. Then, the mixture was heated at reflux for 5.5 hours. After cooling to room temperature, insolubles were separated by filtration and the organic phase was concentrated under reduced pressure. The residue was distilled under reduced pressure to obtain 10.3 g (in a yield of 27%) of the objective compound as a colorless liquid.

$^1$H-NMR (CDC$_3$) 1.03 ppm (s, 6H), 2.27 (s, 12H), 2.53 (t, J=6.0 Hz, 2H), 3.29 (s, 2H), 3.54 (t, J=6.0 Hz, 2H)

Boiling point: 75-77° C./6 mmHg

Example 17

Production of 1,1'-oxybis(N,N,2-trimethylpropane-2-amine)

To tetrahydrofuran (100 mL), oily sodium hydride (purity of 60% by weight, 6.6 g, 99 mmol) was added and then 2-dimethylamino-2-methyl-1-propanol (11.7 g, 99.8 mmol) was added dropwise at 0° C. After heating to reflux, the mixture was stirred for 3 hours. A tetrahydrofuran (25 mL) solution of p-toluenesulfonyl chloride (9.53 g, 50 mmol) was added dropwise at a reflux temperature. Then, potassium iodide (3.75 g, 22.6 mmol) and toluene (100 mL) were added and the mixture was refluxed overnight. After being left standing to cool to room temperature, water was added and the solution was extracted with ethyl acetate. The organic phase was washed with water, dried over an anhydrous magnesium sulfate powder and then concentrated under reduced pressure. The residue was distilled under reduced pressure to obtain 4.69 g (43%) of the objective compound as a colorless liquid.

$^1$H-NMR (CDC$_3$) 1.06 ppm (s, 12H), 2.29 (s, 12H), 3.27 (s, 4H)

Boiling point: 85-88° C./7 mmHg

Example 18

Production of 2-(2-(dimethylamino)ethoxy)-N,N-dimethylcyclohexaneamine

To tetrahydrofuran (100 mL), oily sodium hydride (purity 60% by weight, 18 g, 450 mmol) was added and 2-(dimethylamino)ethanol (16.1 g, 180 mmol) was added dropwise at 0° C., and then the mixture was refluxed for 3 hours. To this suspension, toluene (80 mL) and tetrahydrofuran (25 mL) were added. A toluene (200 mL)/tetrahydrofuran (25 mL) mixed solution of p-toluenesulfonyl chloride (37.2 g, 195 mmol) was added dropwise at 0 to 5° C., followed by stirring at the same temperature for 1 hour. After further stirring for 1 hour under heating at reflux, the mixture was left standing to cool to room temperature. After adding dropwise 2-(dimethylamino)cyclohexanol (21.5 g, 150 mmol) at room temperature, potassium iodide (29.9 g, 180 mmol) was added. After stirring for 9 hours under heating at reflux, the reaction solution was left standing to cool to room temperature. Water was added and the solution was extracted with ethyl acetate, and then the organic phase was washed with water and saturated saline. This organic phase was dried over an anhydrous magnesium sulfate powder and then concentrated under reduced pressure. The residue was distilled under reduced pressure to obtain 2.3 g (in a yield of 7%) of the objective compound as a yellow liquid.

$^1$H-NMR (CDC$_3$) 1.11-1.26 ppm (m, 4H), 1.67-1.78 (m, 3H), 2.09-2.12 (m, 1H), 2.26 (s, 6H), 2.36 (s, 6H), 2.39-2.42

(m, 1H), 2.51 (td, J=6.4, 1.3 Hz, 2H), 3.25 (td, J=9.4, 4.1 Hz, 1H), 3.53 (dt, J=9.5, 6.4 Hz, 1H), 3.68 (dt, J=9.5, 6.4 Hz, 1H)

Boiling point: 91-93° C./5 mmHg

INDUSTRIAL APPLICABILITY

According to the method for producing an organolithium compound of the present invention, it is possible to considerably improve the stability of an organolithium compound produced through metalization by lithium. This method enables the production of an organolithium compound in a high yield under comparatively mild conditions by considerably decreasing the operational burden and the burden of safety measures. Also, according to the method for producing a substituted aromatic compound of the present invention, it is possible to obtain a substituted aromatic compound in a high yield under comparatively mild conditions by considerably decreasing the operational burden and the burden of safety measures. That is, in a tubular flow type reactor such as a microreactor and a cascade method, defects such as occlusion of transfer tubes among a tube, a reactor and a batch are less likely to arise in the continuous reaction under comparatively mild conditions. In the case of a batch type reaction, the generation of scaling of the reactor can be prevented and thus the reaction can be easily controlled. In case very large stabilization effect of an organolithium compound is exerted, continuation per se can be avoided. Furthermore, according to the production method of the present invention, since a special facility is not required for cooling, production costs can be considerably suppressed. In a tubular flow type reactor, since the diameter of the tube can be increased, production costs can be considerably suppressed.

The invention claimed is:
1. A ligand represented by formula (3):

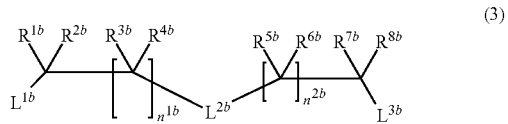

(3)

wherein, in formula (3),
$L^{2b}$ represents —O— or —N(—CH$_2$—R$^{21}$)—,
$R^{21}$ represents a hydrogen atom or a C1-6 alkyl group,
$L^{1b}$ represents —OR$^{22}$ or —N(R$^{23}$)R$^{24}$,
$L^{3b}$ represents —OR$^{221}$ or —N(R$^{231}$)R$^{241}$,
$R^{22}$ and $R^{221}$ each, independently, represents a C1-6 alkyl group,
$R^{23}$ and $R^{231}$ each, independently, represents a methyl group, an ethyl group, or an n-propyl group,
$R^{24}$ and $R^{241}$ each, independently, represents a C1-6 alkyl group (provided that when $L^{2b}$ is —O— and $L^{1b}$ is —OR$^{22}$, $L^{3b}$ is —N(R$^{231}$)R$^{241}$ and, when $L^{2b}$ is —O— and $L^{3b}$ is —OR$^{221}$, $L^{1b}$ is —N(R$^{23}$)R$^{24}$),
$n^{1b}$ and $n^{2b}$ each, independently, represents an integer of 1 to 3,
$R^{1b}$ and $R^{2b}$ represent a C1-6 alkyl group,
$R^{3b}$, $R^{4b}$, $R^{5b}$, $R^{6b}$, $R^{7b}$ and $R^{8b}$ each, independently, represents a hydrogen atom or a C1-6 alkyl group (provided that when $L^{2b}$ is —N—CH$_3$, $L^{1b}$ and $L^{3b}$ is —N(CH$_3$)CH$_3$ and $n^{1b}$ and $n^{2b}$ are 1, $R^{1b}$, $R^{2b}$, $R^{3b}$, $R^{4b}$, $R^{5b}$, $R^{6b}$, $R^{7b}$ and $R^{8b}$ are not simultaneously methyl groups) and a ring may be formed between ($R^{1b}$ or $R^{2b}$) and ($R^{3b}$ or $R^{4b}$) or between ($R^{5b}$ or $R^{6b}$) and ($R^{7b}$ or $R^{8b}$).

* * * * *